US012725690B2

(12) United States Patent
Vaughn et al.

(10) Patent No.: US 12,725,690 B2
(45) Date of Patent: Sep. 1, 2026

(54) REMOTE ADMINISTRATION OF MEDICAL DEVICE TREATMENT

(71) Applicant: Ampa Inc., San Diego, CA (US)

(72) Inventors: Donald A. Vaughn, San Diego, CA (US); Jonathan A.S. Downar, Carrying Place (CA)

(73) Assignee: AMPA INC., San Diego, CA (US)

( * ) Notice: Subject to any disclaimer, the term of this patent is extended or adjusted under 35 U.S.C. 154(b) by 0 days.

(21) Appl. No.: 18/542,233

(22) Filed: Dec. 15, 2023

(65) Prior Publication Data

US 2025/0201371 A1 Jun. 19, 2025

(51) Int. Cl.

*G16H 20/10* (2018.01)
*G16H 10/60* (2018.01)
*G16H 40/40* (2018.01)
*G16H 40/67* (2018.01)

(52) U.S. Cl.

CPC ............. *G16H 20/10* (2018.01); *G16H 10/60* (2018.01); *G16H 40/40* (2018.01); *G16H 40/67* (2018.01)

(58) Field of Classification Search

CPC ......... G16H 10/60; G16H 40/40; G16H 40/67
USPC .......................................... 600/9–15; 607/45
See application file for complete search history.

(56) References Cited

U.S. PATENT DOCUMENTS 6,425,852 B1 * 7/2002 Epstein ................. A61N 2/006 600/15
9,724,533 B1 8/2017 Fischell et al. ........ A61N 2/008
9,968,798 B2 5/2018 Fischell et al. .......... A61N 2/02
10,004,915 B2 6/2018 Saitoh et al. ............ A61N 2/02
10,029,112 B1 7/2018 Fischell et al. ........ A61N 2/008
10,137,308 B2 11/2018 Adjouadi et al. ...... A61N 2/006
10,507,335 B2 12/2019 Zrenner et al. .......... A61N 2/02
11,367,519 B1 * 6/2022 Heldman ............. A61M 5/142
2011/0118809 A1 * 5/2011 Rossi ................ A61N 1/37282 607/63
2015/0196775 A1 * 7/2015 McMillan ........... A61N 5/0616 607/88

(Continued)

OTHER PUBLICATIONS

Blumberger et al., “Effectiveness of theta burst versus high-frequency repetitive transcranial magnetic stimulation in patients with depression (THREE-D): a randomized non-inferiority trial” *The Lancet,* Apr. 28, 2018, abstract only, 18 pages.

(Continued)

*Primary Examiner* — John R Downey
(74) *Attorney, Agent, or Firm* — HAYES SOLOWAY P.C.

(57) ABSTRACT

A system for administering treatment with a medical device includes a medical device capable of delivering a medical treatment to a patient. An electronic computing device has a processor, computer-readable memory, and a power supply. The electronic computing device is in communication with the medical device. A patient interface is in communication with the electronic computing device and the medical device. The electronic computing device is configured to: receive an initial electronic treatment protocol; communicate the initial electronic treatment protocol to the medical device to enable an initial treatment of the patient; receive patient input through the patient interface; receive an updated treatment protocol based on the patient input; and communicate the updated treatment protocol to the medical device to enable an updated treatment of the patient.

19 Claims, 9 Drawing Sheets

(56) References Cited

U.S. PATENT DOCUMENTS

2019/0126055 A1* 5/2019 Etkin .................... A61B 5/372
2019/0290928 A1* 9/2019 Biginton .................. A61N 2/02
2019/0351248 A1 11/2019 Murphy et al.
2020/0289837 A1* 9/2020 Lowin .................... A61N 2/006
2021/0196971 A1* 7/2021 Lowin ...................... A61N 2/12
2021/0225514 A1* 7/2021 Lin ........................ G16H 40/63
2021/0280286 A1* 9/2021 Ravindranathan .......................... A61N 1/36021
2022/0134119 A1* 5/2022 McDonald ......... A61N 1/37247 607/46
2022/0400952 A1* 12/2022 Srivastava ........... A61B 5/4824

OTHER PUBLICATIONS

Calabrò, Rocco Salvatore, et al. "Applications of Transcranial Magnetic Stimulation in Migraine: Evidence from a Scoping Review." Journal of Integrative Neuroscience, vol. 21, No. 4, Jun. 2022, p. 110, https://doi.org/10.31083/j.jin2104110.

Cole, Eleanor J., et al. "Stanford Neuromodulation Therapy (SNT): A Double-Blind Randomized Controlled Trial." The American Journal of Psychiatry, vol. 179, No. 2, Feb. 2022, pp. 132-141, https://doi.org/10.1176/appi.ajp.2021.20101429.

Chen, Gengbin, et al. "Effects of Repetitive Transcranial Magnetic Stimulation on Upper-Limb and Finger Function in Stroke Patients: A Systematic Review and Meta-Analysis of Randomized Controlled Trials." Frontiers in Neurology, vol. 13, Jul. 2022, p. 940467, https://doi.org/10.3389/fneur.2022.940467.

Carmi, Lior, et al. "Efficacy and Safety of Deep Transcranial Magnetic Stimulation for Obsessive-Compulsive Disorder: A Prospective Multicenter Randomized Double-Blind Placebo-Controlled Trial." The American Journal of Psychiatry, vol. 176, No. 11, Nov. 2019, pp. 931-938, https://doi.org/10.1176/appi.ajp.2019.18101180.

Cox, Jessika, et al. "Repetitive Transcranial Magnetic Stimulation for Generalized Anxiety and Panic Disorders: A Systematic Review and Meta-Analysis." Annals of Clinical Psychiatry: Official Journal of the American Academy of Clinical Psychiatrists, vol. 34, No. 2, May 2022, pp. e2-24, https://doi.org/10.12788/acp.0050.

Dalton, Bethan, et al. "A Pilot Study Exploring the Effect of Repetitive Transcranial Magnetic Stimulation (rTMS) Treatment on Cerebral Blood Flow and Its Relation to Clinical Outcomes in Severe Enduring Anorexia Nervosa." Journal of Eating Disorders, vol. 9, No. 1, Jul. 2021, p. 84, https://doi.org/10.1186/s40337-021-00420-w.

Dunlop, Katharine, et al. "Increases in Frontostriatal Connectivity Are Associated with Response to Dorsomedial Repetitive Transcranial Magnetic Stimulation in Refractory Binge/purge Behaviors." NeuroImage: Clinical, vol. 8, Jan. 2015, pp. 611-618, https://doi.org/10.1016/j.nicl.2015.06.008.

Elmaghraby, Rana, et al. "A Systematic Review of the Safety and Tolerability of Theta Burst Stimulation in Children and Adolescents." Neuromodulation: Journal of the International Neuromodulation Society, vol. 25, No. 4, Jun. 2022, pp. 494-503, https://doi.org/10.1111/ner.13455.

Feffer, Kfir, et al. "Dorsomedial Prefrontal rTMS for Depression in Borderline Personality Disorder: A Pilot Randomized Crossover Trial." Journal of Affective Disorders, vol. 301, Mar. 2022, pp. 273-280, https://doi.org/10.1016/j.jad.2021.12.038.

Feng, Yali, et al. "Effects of Non-Invasive Brain Stimulation on Headache Intensity and Frequency of Headache Attacks in Patients with Migraine: A Systematic Review and Meta-Analysis." Headache, vol. 59, No. 9, Oct. 2019, pp. 1436-1447, https://doi.org/10.1111/head.13645.

Fitzsimmons, Sophie M. D. D., et al. "Repetitive Transcranial Magnetic Stimulation for Obsessive-Compulsive Disorder: A Systematic Review and Pairwise/network Meta-Analysis." Journal of Affective Disorders, vol. 302, Apr. 2022, pp. 302-312, https://doi.org/10.1016/j.jad.2022.01.048.

Folmer, Robert L., et al. "Repetitive Transcranial Magnetic Stimulation Treatment for Chronic Tinnitus: A Randomized Clinical Trial." JAMA Otolaryngology—Head & Neck Surgery, vol. 141, No. 8, Aug. 2015, pp. 716-722, https://doi.org/10.1001/jamaoto.2015.1219.

Gay, F., et al. "Neuromodulation Treatments of Pathological Anxiety in Anxiety Disorders, Stressor-Related Disorders, and Major Depressive Disorder: A Dimensional . . . " Frontiers in, 2022, https://www.frontiersin.org/articles/10.3389/fpsyt.2022.910897/pdf.

Gholami, Mehrnaz, et al. "Evaluation of rTMS in Patients with Poststroke Aphasia: A Systematic Review and Focused Meta-Analysis." Neurological Sciences: Official Journal of the Italian Neurological Society and of the Italian Society of Clinical Neurophysiology, vol. 43, No. 8, Aug. 2022, pp. 4685-4694, https://doi.org/10.1007/s10072-022-06092-x.

Harris, Adam, and John Reece. "Transcranial Magnetic Stimulation as a Treatment for Posttraumatic Stress Disorder: A Meta-Analysis." Journal of Affective Disorders, vol. 289, Jun. 2021, pp. 55-65, https://doi.org/10.1016/j.jad.2021.04.003.

Hu, Yueqing, et al. "Efficacy and Safety of Simultaneous rTMS-tDCS over Bilateral Angular Gyrus on Neuropsychiatric Symptoms in Patients with Moderate Alzheimer's Disease: A Prospective, Randomized, Sham-Controlled Pilot Study." Brain Stimulation, vol. 15, No. 6, Nov. 2022, pp. 1530-1537, https://doi.org/10.1016/j.brs.2022.11.009.

Koch, Giacomo, et al. "Precuneus Magnetic Stimulation for Alzheimer's Disease: A Randomized, Sham- Controlled Trial." Brain: A Journal of Neurology, vol. 145, No. 11, Nov. 2022, pp. 3776-3786, https://doi.org/10.1093/brain/awac285.

Liang, Zhengrong, et al. "Repetitive Transcranial Magnetic Stimulation on Chronic Tinnitus: A Systematic Review and Meta-Analysis." BMC Psychiatry, vol. 20, No. 1, Nov. 2020, p. 547, https://doi.org/10.1186/s12888-020-02947-9.

Mishra, Archana, et al. "Effect of Repetitive Transcranial Magnetic Stimulation on Seizure Frequency and Epileptiform Discharges in Drug-Resistant Epilepsy: A Meta-Analysis." Journal of Clinical Neurology , vol. 16, No. 1, Jan. 2020, pp. 9-18, https://doi.org/10.3988/jcn.2020.16.1.9.

Sigrist, Christine, et al. "Transcranial Magnetic Stimulation in the Treatment of Adolescent Depression: A Systematic Review and Meta-Analysis of Aggregated and Individual-Patient Data from Uncontrolled Studies." European Child & Adolescent Psychiatry, Jun. 2022, https://doi.org/10.1007/s00787-022-02021-7.

Sun, Nianyi, et al. "The Effect of Repetitive Transcranial Magnetic Stimulation for Insomnia: A Systematic Review and Meta-Analysis." Sleep Medicine, vol. 77, Jan. 2021, pp. 226-237, https://doi.org/10.1016/j.sleep.2020.05.020.

Sun, Wei, et al. "Low-Frequency Repetitive Transcranial Magnetic Stimulation for the Treatment of Refractory Partial Epilepsy: A Controlled Clinical Study." Epilepsia, vol. 53, No. 10, Oct. 2012, pp. 1782-1789, https://doi.org/10.1111/j.1528-1167.2012.03626.x.

Ward, Heather Burrell, et al. "Borderline Personality Traits Do Not Influence Response to TMS." Journal of Affective Disorders, vol. 281, Feb. 2021, pp. 834-838, https://doi.org/10.1016/j.jad.2020.11.054.

Woodside, D. Blake, et al. "A Pilot Trial of Repetitive Transcranial Magnetic Stimulation of the Dorsomedial Prefrontal Cortex in Anorexia Nervosa: Resting fMRI Correlates of Response." Journal of Eating Disorders, vol. 9, No. 1, Apr. 2021, p. 52, https://doi.org/10.1186/s40337-021-00411-x.

* cited by examiner

REMOTE ADMINISTRATION OF MEDICAL DEVICE TREATMENT

FIELD OF THE DISCLOSURE

The present disclosure is generally related to medical device treatment and more particularly is related to administration of medical device treatment. The disclosure has particular utility in the field of transcranial neuromodulation treatment such as transcranial magnetic stimulation (TMS) of a patient and will be described in particular with such utility, although other utilities are contemplated including but not limited to transcranial electrical stimulation (TES), focused ultrasound (FUS), electroencephalography (EEG), magnetoencephalography (MEG), photobiomodulation, and near infrared spectroscopy (NIRS), which are given as exemplary but not limitation.

BACKGROUND OF THE DISCLOSURE

Modern medical devices allow medical providers to deliver therapeutic and preventative treatments to patients under close medical supervision. Such devices comprise a wide range of therapies and care areas, including cosmetic devices, pediatric devices, cardiovascular devices, home health monitors and devices, neurological devices, and the like. Typically, these devices are operated by trained providers who are certified to use the devices and administer a treatment. In some cases, the devices are operated by licensed medical practitioners and treatments are provided as a controlled prescription.

One issue with receiving treatment through these medical devices is that patients are limited by geography, time, and the availability of care provider-personnel involved in the preparation, delivery, oversight, administration, orchestration, or coordination of medical care. Patients receiving treatment may be required to travel long distances to care provider locations in order to receive treatment. Patients may be required to wait for treatment until care provider business hours or until availability in a provider's schedule. And patients may be required to receive treatment only from providers located within the patient's city, state, or country. All of these restrictions serve to limit patients' access to treatment.

Remote administration of treatment using medical devices is limited, and suffers from a number of problems. Certain devices may be hardcoded with restrictions on use, for instance, to a particular number of uses over a time period, which may limit the efficacy of the treatment for the patient. Other devices may receive use or prescription updates from practitioners who may not have access to the patient's most current medical information. This makes it difficult for providers to prescribe effective treatment as patient use of the medical device progresses.

Another issue with receiving treatments through these medical devices is that treatment may cause significant discomfort while being administered. If discomfort is too great, patients may avoid treatment, delay sessions, end sessions early, or otherwise fail to receive the necessary amount of treatment. Providers can use subjective measures for sensing discomfort in order to adjust the treatment parameters. However, providers cannot always devote suitable attention to patient comfort while administering treatment, and they may not always accurately assess patient comfort levels during each session.

Thus, a heretofore unaddressed need exists in the industry to address the aforementioned deficiencies and inadequacies.

SUMMARY OF THE DISCLOSURE

Embodiments of the present disclosure provide a system and method for administering treatment with a medical device. Briefly described, in architecture, one embodiment of the system, among others, can be implemented as follows. A system for administering treatment with a medical device includes a medical device capable of delivering a medical treatment to a patient. An electronic computing device has a processor, computer-readable memory, and a power supply. The electronic computing device is in communication with the medical device. A human interface is in communication with the electronic computing device and the medical device. The electronic computing device is configured to: receive an initial electronic treatment protocol; communicate the initial electronic treatment protocol to the medical device to enable an initial treatment of the patient: receive communication from the medical device; receive human input through the human interface; and optionally internally generate or receive from a server over at least one network connection an updated treatment protocol; and communicate the updated treatment protocol to the medical device to enable an updated treatment of the patient.

In one aspect of the system, at least one sensor is in communication with the electronic computing device. In another aspect of the system, the electronic computing device is configured to communicate device treatment records or human interface data generated by the electronic computing device to a care provider's computing device over at least one network connection. In yet another aspect of the system, the electronic computing device is configured to transfer the internally generated updated treatment protocol to at least one server, over at least one network connection to a care provider's computing device. In a particular aspect of the system, the at least one sensor is at least one from the set of: an imaging device, a microphone, a pulse oximeter, an electrocardiogram, an electromyogram, a contact sensor, a gyroscope, functional near infrared spectroscopy, focused ultrasound, and electroencephalogram electrodes. In another particular aspect of the system, the electronic computing device is further configured to communicate patient biological data acquired by the at least one sensor to a care provider's computing device over at least one network connection. In another particular aspect of the system, the updated treatment protocol is additionally determined based on the patient biological data acquired by at least one sensor. In another particular aspect of the system, the updated treatment protocol is additionally determined based on at least one of the Electronic Medical Records of the patient or other patients.

In one aspect of the system the Electronic Medical Records are located, partially or fully, on at least one of the following: the electronic computing device, or at least one server over which the electronic computing device is in communication over at least one network connection. In another aspect of the system, the Electronic Medical Records is composed at least one from the set of: patient biological data acquired by at least one sensor, treatment records produced by the electronic computing device, data gathered from the human interface, or data from an Electronic Medical Record system.

In another aspect of the system, the electronic computing device is physically incorporated into the medical device.

The present disclosure can also be viewed as providing methods of administering treatment with a medical device. In this regard, one embodiment of such a method, among others, can be broadly summarized by the following steps: receiving, on an electronic computing device having a processor, computer-readable memory, and a power supply, an initial electronic treatment protocol corresponding to a medical device capable of delivering a medical treatment to a patient; communicating the initial electronic treatment protocol to the medical device to enable an initial treatment of the patient; receiving, through a patient interface in communication with the electronic computing device, a human input; and optionally internally generating or receiving from a server over at least one network connection by the electronic computing device, an updated treatment protocol; and communicating the updated treatment protocol to the medical device to enable an updated treatment of the patient.

In one aspect of the method, the patient input comprises patient-reported data, including a collateral historian, an operator of the medical device, or a care provider. In one aspect of the method the protocol update process occurs on the electronic computing device, or on at least one server that is in communication with the electronic device over at least one network connection.

Another aspect of the method further comprises the step of receiving, by the electronic computing device, patient biological data captured by at least one sensor, and wherein the updated treatment protocol is based on patient biological data. A particular aspect of the method further comprises the step of receiving, over at least one network connection, patient Electronic Medical Records, and wherein the updated treatment protocol is based on Electronic Medical Records. In another particular aspect of the method, the at least one sensor is at least one from the set of: an imaging device, a microphone, a pulse oximeter, an electrocardiogram, an electromyogram, a contact sensor, a gyroscope, functional near infrared spectroscopy, focused ultrasound, and electroencephalogram electrodes. Another particular aspect of the method further comprises the step of remotely observing, by a care provider during, and/or after administration of the initial treatment, the patient biological data captured by the at least one sensor. Another particular aspect of the method further comprises the step of communicating, by the care provider and over at least one network connection, with the patient before, during and/or after remote observation of the initial treatment.

In another aspect of the method, the updated treatment protocol is updated in real-time as the treatment or preparatory procedure is being performed—an example of which is a calibration procedure like a motor-threshold or neurocardiac threshold determination.

In another aspect of the method, the updated treatment protocol is determined by an algorithmic expression.

In another aspect of the method, the updated treatment protocol is determined by a care provider and communicated to the electronic computing device using the care provider's computing device.

The present disclosure can also be viewed as providing methods of administering treatment of transcranial neuromodulation. In this regard, one embodiment of such a method, among others, can be broadly summarized by the following steps: receiving, over a communications network, an electronic treatment protocol to a medical device capable of delivering transcranial neuromodulation to the human patient; initiating the electronic treatment protocol on the human patient; performing the electronic treatment protocol on the human patient according to at least one prescription parameter; and concluding the electronic treatment protocol.

In one aspect of the method, at least a portion of the electronic treatment protocol is controlled remotely over the communications network by a remote provider.

In another aspect of the method, the at least one prescription parameter is selected from the set of: patient authentication, device authentication, operator authentication, location authentication, delivery schedule, session numbers, delivery hardware, stimulation target location, stimulation target rotation, stimulation intensity, stimulation pattern, pulse waveform, angle of incidence, sensor target location(s), sensor target rotations, sensor sampling rate, wavelength(s), carrier frequency, sensor type, assessment schedule, and assessment type(s).

The present disclosure can also be viewed as providing methods of administering brain energy treatment such as transcranial neuromodulation. In this regard, one embodiment of such a method, among others, can be broadly summarized by the following steps: receiving an initial electronic treatment protocol to a medical device capable of delivering transcranial neuromodulation to the human patient; performing the initial electronic treatment protocol on the human patient; by the medical device, modulating the initial electronic treatment protocol to modify at least one from the set of: pulse amplitude, pulse sequence timing, total number of pulses, and stimulation location to create a subsequent electronic treatment protocol, wherein the modulation of the initial electronic treatment protocol is determined by at least one from the set of: measures of patient discomfort and values from treatment history; and receiving the subsequent electronic treatment protocol to the medical device capable of delivering transcranial neuromodulation to the patient; and performing the subsequent electronic treatment protocol on the patient, or communicating the subsequent electronic treatment protocol to the medical device to enable subsequent treatment of the patient; and initiate the subsequent electronic treatment protocol with the patient, or communicating the subsequent electronic treatment protocol to the medical device to enable subsequent treatment of the patient; and performing the subsequent electronic treatment protocol on the patient.

In one aspect of the method, the initial electronic treatment protocol is determined by at least one from the set of: a starting amplitude, a minimum therapeutic amplitude, a target amplitude, pulse sequence timing, and stimulation location.

In another aspect of the method, the measures of human patient discomfort are at least one taken from the set of: patient biological signals and discomfort ratings scales. In a particular aspect of the method, the human patient biological signals are at least one from the set of: neural activity, facial expressions, vocalizations, and blood flow.

In another aspect of the method, the values from treatment history are at least one taken from the set of: pulse amplitude, pulse sequence timing, total number of pulses, and stimulation target.

The present disclosure can also be viewed as providing a system for administering modulated treatment with a medical device. Briefly described, in architecture, one embodiment of the system, among others, can be implemented as follows. A system for administering modulated treatment with a medical device includes a medical device capable of delivering a medical treatment to a patient. An electronic computing device has a processor, computer-readable memory, and a power supply. The electronic computing device is in communication with the medical device. The electronic computing device is configured to: receive an initial electronic treatment protocol; communicate the initial electronic treatment protocol to the medical device to enable an initial treatment of the patient; initiate the initial electronic treatment protocol with the patient; modulate the initial electronic treatment protocol to create a subsequent electronic treatment protocol, wherein the modulation of the initial electronic treatment protocol is determined by at least one from the set of: measures of patient discomfort and values from treatment history; communicate the subsequent electronic treatment protocol to the medical device to enable subsequent treatment of the patient; and initiate the subsequent electronic treatment protocol with the patient.

The present disclosure can also be viewed as providing methods of administering modulated treatment with a medical device. In this regard, one embodiment of such a method, among others, can be broadly summarized by the following steps: receiving, on an electronic computing device having a processor, computer-readable memory, and a power supply, an initial electronic treatment protocol corresponding to a medical device capable of delivering a medical treatment to a patient: communicating the initial electronic treatment protocol to the medical device to enable an initial treatment of the patient; performing the initial electronic treatment protocol on the patient; by the electronic computing device, modulating the initial electronic treatment protocol to create a subsequent treatment protocol, where the modulation of the initial electronic treatment protocol is determined by at least one from the set of: measures of patient discomfort and values from treatment history; communicating the subsequent electronic treatment protocol to the medical device to enable subsequent treatment of the patient; and performing the subsequent electronic treatment protocol with the patient. Other systems, methods, features, and advantages of the present disclosure will be or become apparent to one with skill in the art upon examination of the following drawings and detailed description.

It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

As used herein the term "patient" shall mean a human animal or a non-human animal.

As used herein "care provider" may be a health care professional such as medical staff personnel, technician, nurse or physician, or a caretaker, a companion, or family member, or a service organization such as a hospital, physician group, or diagnostics facility.

Also, the term "remote treatment" may comprise treatments provided in remote settings, as well as treatments provided within traditional facilities, but where not all involved patient(s), personnel, apparatuses, and algorithms are co-located in time & space, much like 'remote viewing' or 'remote control' indicate distance but not that one person is in a remote part of the world, far from urban centers.

And, the term "human interface" may include direct patient interaction as well as patient interaction through another including a collateral historian, i.e., a person who knows the patient and answers for the patient or through a device.

"Electronic Medical Records" (EMRs) are defined as comprehensive digital records of a patient's health information and medical history, encompassing data such as medical and treatment history (past and present illnesses, treatments, surgeries, allergies, medications), diagnostic data (results from lab tests, X-rays, MRIs, CT scans), treatment records (details of treatments, prescriptions, surgical procedures, follow-up care, and specifically including all data collected by the electronic computing device described in this disclosure—e.g. pulses delivered and all their corresponding data, discomfort ratings, movement responses during mapping sessions, etc.), personal and insurance information (patient's name, date of birth, contact information, possibly next of kin), progress notes (observations by healthcare professionals), vital signs and physical examination findings (blood pressure, heart rate, temperature, examination results), immunization records (history of vaccinations), and relevant lifestyle information (details about lifestyle factors like smoking, alcohol use, exercise, diet).

Figure 1:
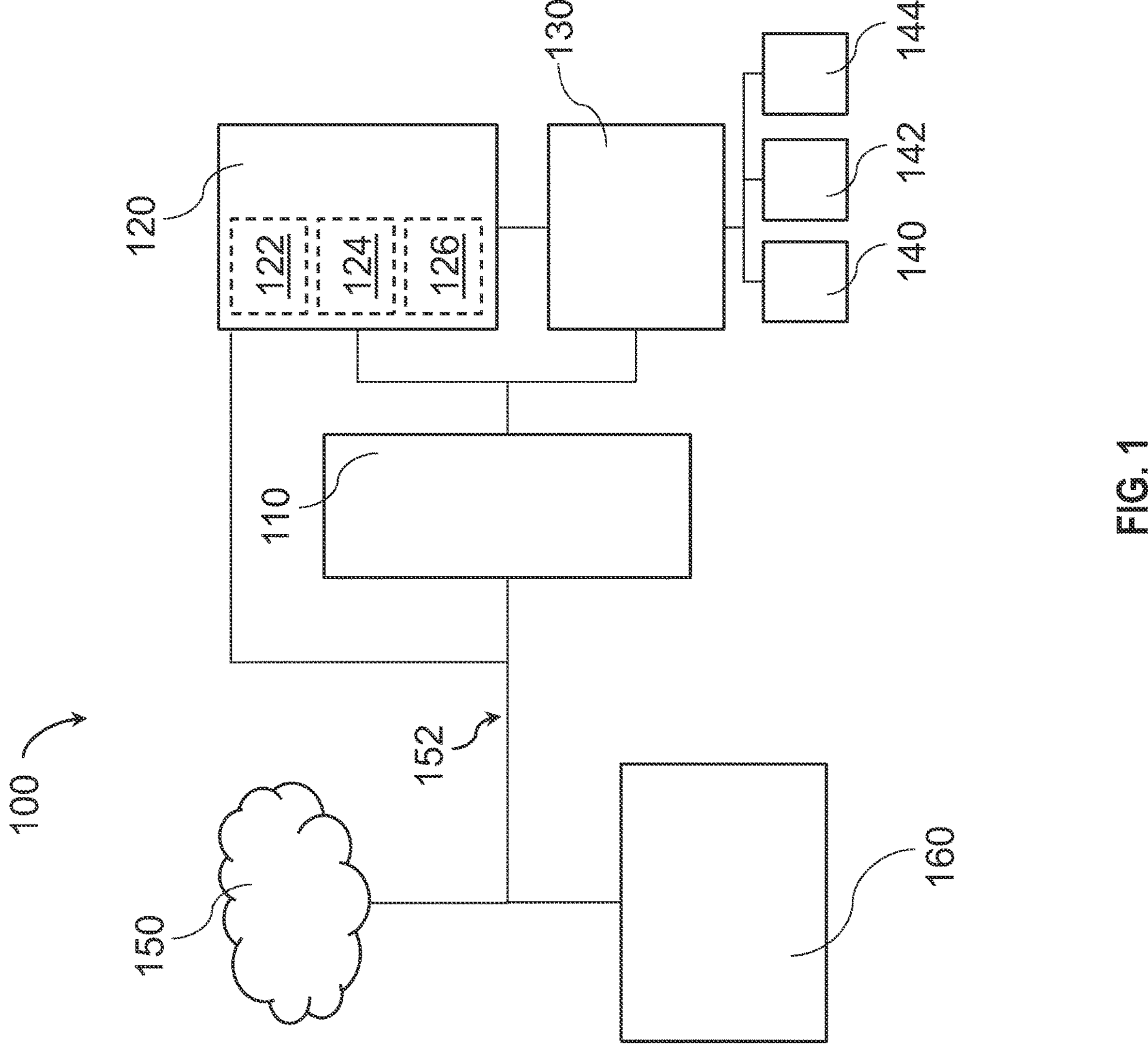
FIG. 1 is a diagrammatic illustration of a system for administering remote treatment with a medical device, in accordance with a first exemplary embodiment of the present disclosure.

FIG. 1 is a diagrammatic illustration of a system for administering treatment with a medical device, in accordance with a first exemplary embodiment of the present disclosure. The system for administering remote treatment with a medical device ("system") 100 includes a medical device 110 capable of delivering a medical treatment to a patient. An electronic computing device 120 has a processor 122, computer-readable memory 124, and a power supply 126. The electronic computing device 120 is in communication with the medical device 110. A patient interface 130 is in communication with the electronic computing device 120 and the medical device 110. The electronic computing device 120 is configured to: receive an initial electronic treatment protocol; communicate the initial electronic treatment protocol to the medical device 110 to enable an initial treatment of the patient; receive patient input through the patient interface 130; receive an updated treatment protocol based on the patient input; and communicate the updated treatment protocol to the medical device 110 to enable an updated treatment of the patient.

The medical device 110 may be any device capable of being electronically controlled to deliver a therapeutic treatment to a patient. This may include devices across a number of practice areas, including cosmetic, pediatric, cardiovascular, home health, neurological, and overweight and obesity devices. For example, cosmetic medical devices may include skin treatment devices, such as laser-based and abrasion devices, microneedling devices, dermal fillers, and the like. Pediatric medical devices may include SIDS prevention and monitoring devices, such as wearable monitors, bassinets, sensor arrays, and the like. Cardiovascular medical devices may include pacemakers, defibrillators, and the like. Home health medical devices may include blood glucose testers and monitors, self-applied disease tests, such as at-home COVID tests, electronic muscle stimulators, hearing aids, and the like. Neurological medical devices may include implanted brain-computer interface devices, transcranial magnetic stimulation devices, and the like. Overweight and obesity medical devices may include electrical stimulation systems, food intake monitors, and the like. This list is offered as an illustrative example, and is not intended to be exhaustive or limiting.

Medical devices 110 coming within the scope of this disclosure may be electronically controllable, which is to say may be controlled to operate by an electronic controller, whether internal or external. The electronic control may govern whether the medical device 110 is in an operational state (on/off), when treatment is delivered, and what treatment is delivered. This is described in greater detail relative to FIG. 3, below. The treatment delivered may vary depending on the medical device 110, but may generally include the delivery of electrical or magnetic pulses, mechanical stimulation, chemical compounds, and the like. The treatment may also include receiving data from the patient, including patient vital information, blood content levels, bioelectrical data, and the like.

In one example, more than one medical device 110 may be used. For instance, a patient may use a medical device 110 for treatment at home, and may use another of the same type of medical device 110 for treatment while traveling. In another case, the patient may use one type of medical device 110 for one type of treatment, and another type of medical device 110 for another type of treatment. In another example, multiple patients may use the same medical device 110. For instance, all the members of a family may use a single medical device 110 to receive treatments at different times. Each family member may have a patient identifier or user account allowing for different treatments to be assigned to each family member.

A patient may be any entity receiving the therapeutic treatment, including persons formally in a physician-patient relationship, persons outside of a formal physician-patient relationship, and other living creatures, such as animals. In one example, the patient may be considered a user of the medical device 110 and may operate it, at least in part, to deliver treatment. In another example, the patient may not control the operation of the medical device 110, but may position the medical device 110 to interact with the patient's body as needed.

A medical device 110 capable of delivering a medical treatment to a patient may be defined as a medical device 110 that, in operation, may provide a treatment as described above.

The electronic computing device 120 may be any suitable type, number, and configuration of computing devices. In one example, the electronic computing device 120 may be part of the medical device 110, i.e., may be manufactured together as part of the medical device unit, and may be housed together with the other operative components of the medical device 110. In another example, the electronic computing device 120 may be separate from the medical device 110. This may include, for example, personal computers, such as desktops, laptops, netbooks, and the like, as well as mobile devices, such as smart phones, tablets, smart displays, smartwatches, smart glasses, and the like. This may further include standalone electronic computing devices 120 manufactured specifically to operate with the medical device 110 or with a mobile device, for instance, as a peripheral device, as well as general-purpose peripheral devices configured to operate with a mobile device or medical device 110. The electronic computing device 120 may be in communication with the medical device 110, for example, by direct wired connection, wireless connections such as Wi-Fi®, Bluetooth®, Near-Field Communication, and the like. In one example, the electronic computing device 120 may access the Internet, local area networks, wide area networks, wireless area networks, or other types of communications networks.

The electronic computing device 120 may Include a processor 122, computer-readable memory 124, power supply 126, and any other components necessary to operate and communicate as described herein. For example, this may further include network access components, specialized processing units, user interfaces, input and output ports, and the like. The power supply 126 may include wired power, such as alternating current delivered through wall outlets, battery power, and the like.

The electronic computing device 120 may be configured to control the operation of the medical device 110. This may include direct control, wherein the electronic computing device 120 may provide instructions directly to the operating components of the medical device 110 to engage in treatment, as well as indirect control, wherein the electronic computing device 120 may communicate instructions to a controller within the medical device 110. In one example, the electronic computing device 120 may be in communication with the medical device 110 indirectly, for instance, through a server 150 over a communications network 152 such as the Internet. In such a case, operation of the electronic computing device 120 may cause the server 150 to send instructions to the medical device 110 to operate.

A patient interface 130 is in communication with the electronic computing device 120. This may include a physical patient interface, comprising buttons, switches, keys, knobs, dials, and the like, or a digital patient interface, comprising graphical, audio, or tactile elements, or any combination thereof. In one example, a graphical user interface may be displayed on the medical device 110 or on the electronic computing device 120. This may include the display and operation of a software application run by the medical device 110 or electronic computing device 120, for instance, as an app on the patient's mobile device. In one example, the patient may operate the patient interface 130 to cause the medical device 110 to administer treatment. For instance, the patient interface 130 may allow the patient to turn on the medical device 110, select a treatment, and begin receiving treatment at a desired time.

In one example, the patient interface 130 may be a plurality of interfaces that may be located on or observed with any combination of the medical device 110 and the electronic computing device. For instance, the medical device 110 may include a patient interface 130 comprising physical hardware and a graphical interface, and the electronic computing device may include a patient interface 130 comprising a graphical interface. The plurality of interfaces may operate together to allow the patient to operate the medical device 110 and to accept input from the patient.

The patient interface 130 may also accept input from the patient. This input may be in any suitable form, and may be provided directly or indirectly from the patient. For instance, the patient interface 130 may allow the patient to enter data or select preferences by operating physical interface components, typing text into a form, selecting options displayed on a graphical interface, and the like. Such data may include information relevant to the treatment being provided, such as the patient's medical history, current medical information, whether the patient is experiencing pain, and the like. For instance, a patient preparing to use a TENS unit for muscle stimulation may first use the patient interface 130 to provide information concerning where the patient has had muscle soreness, how frequently the soreness occurs, what rating the patient would give the soreness, and the like. This information may be received by the patient interface 130, communicated to the electronic computing device 120, and considered in providing treatment to the patient.

In another example, the patient interface 130 may allow the patient to enter data or select preferences during treatment. For instance, the patient may select a menu option to indicate that the treatment is too painful or should be adjusted to another part of the patient's body. Or the patient may select a menu option to indicate that the treatment should be increased or otherwise altered. In another example, the patient may provide diagnostic feedback during treatment to indicate whether and to what degree the treatment may be having an effect.

In another example, the patient interface 130 may allow the patient to enter data or select preferences after a round of treatment has been completed. This may include any of the examples discussed above. The data provided through the patient interface 130 after the round of treatment has been completed may be communicated to the electronic computing device 120 and may be considered in providing the next round of treatment to the patient.

In one example, the patient interface 130 may allow patient diagnostic and other data to be indirectly provided to the electronic computing device before, during, and after a round of treatment. The patient interface 130 may include sensors 140, 142, 144 that may operate to gather patient data and communicate it to the electronic computing device 120. The sensors 140, 142, 144 may be any number and combination of sensors capable of gathering biometric or other patient data, including video sensors, temperature sensors, bioelectrical sensors, audio sensors, environment sensors, biometric sensors, and the like. The data gathered may be any data relevant to a patient's treatment, including, but not limited to, the following types of data: optical, from any portion of the spectrum, for instance, visible, infrared, and ultraviolet, audio, heart rate, blood oxygen, breathing rate, cardiographic, body temperature, and the like. Environmental data gathered may include temperature, humidity, ambient noise, ambient light levels, and the like. These lists are provided as examples, and are not intended to be exhaustive.

The data gathered by the sensors 140, 142, 144 may be communicated to the electronic computing device 120. In one example, the electronic computing device 120 may communicate the data to another device, such as the server 150 or to a care provider computing device 160 over at least one communications network. The care provider computing device 160 may be any computing device as described above and operated, monitored, or programmed by a medical care provider. The data may be used by the electronic computing device 120, server 150, or care provider computing device 160 to update or adjust the treatment course for the patient. This updating or adjustment may be performed before a treatment session begins, in real-time during treatment in response to the data, or after treatment in response to the data.

In one example, the sensors 140, 142, 144 may allow a care provider or care provider software to observe the treatment in real-time as it is administered. For example, a camera and microphone may allow a remote care provider to see and hear the patient as they are receiving treatment from the medical device 110. The remote care provider may make notes about what they perceive while the treatment is being performed, and even make adjustments during the treatment session based on their observations. In one particular example, the electronic computing device 120 and/or the care provider computing device 160 may include any combination of cameras and speakers, which may allow the care provider and the patient to communicate visually and/or by audio during the treatment session. This may allow the care provider to request patient feedback by simply asking questions rather than soliciting a response through a graphic interface. In another example, care provider software may receive and observe data related to the treatment as it is administered. The care provider software may be one or more software programs located on the server 150 or the care provider computing device 160 and may be configured to analyze the received data. In one particular example, the care provider software may be configured to adjust the treatment protocol during or after the treatment session based on the analyzed data. The care provider software may, in one example, create a suggested treatment adjustment and communicate it to the care provider for approval. In another example, the care provider software may automatically adjust the treatment according to rules programmed within the software, without review by a human care provider.

In operation, the electronic computing device 120 is configured to control and/or govern the functioning of the medical device 110, either directly or indirectly. During one point of operation, the electronic computing device 120 may be configured to receive an initial electronic treatment protocol. The initial electronic treatment protocol may be digital instructions for the administration of a treatment, i.e., machine-readable code that communicates the treatment protocol to the medical device 110 or governs the operation of the medical device 110. This initial electronic treatment protocol may be received on the electronic computing device 120 either upon manufacture/creation of the software, or it may be downloaded to the electronic computing device 120 from the server 150 or the care provider computing device 160. The point of download may be any suitable input method, including reading from an external memory, such as a USB drive or flash storage, reading from a disc, or download over a wired or wireless communications network.

In one example, the initial electronic treatment protocol may be determined by a provider, such as a physician overseeing the patient's treatment. The initial electronic treatment protocol may be determined by any combination of factors at the discretion of the care provider, such as the patient's medical history, characteristics of the patient's condition and symptoms, characteristics of the medical device 110, and the like. In another example, the initial electronic treatment protocol may be determined by a regulatory body and may be authorized by the care provider. In another example, the initial electronic treatment protocol may be determined by the manufacturer of the medical device 110.

During another point of operation, the electronic computing device 120 may be configured to communicate the initial electronic treatment protocol to the medical device 110 to enable an initial treatment of the patient. The electronic computing device 120 may either communicate the machine-readable code for the medical device 110 to receive, or it may communicate electronic instructions for the medical device 110 to perform according to the initial electronic treatment protocol. The medical device 110 may operate or be operated according to this protocol.

During another point of operation, the electronic computing device 120 may be configured to receive patient input through the patient interface 130. As described above, the patient input may include information given by the patient, data collected by sensors, and the like. In one example, the electronic computing device 120 may further be configured to receive patient medical records in the form of Electronic Medical Records (EMR) and other medical data.

During another point of operation, the electronic computing device 120 may be configured to receive an updated treatment protocol based on the patient input. In one example, the electronic computing device 120 may analyze the patient input and may itself update the treatment protocol. In another example, the electronic computing device 120 may communicate the patient input, as well as diagnostic data regarding operation of the medical device 110, to a server 150 or care provider computing device 160 over at least one network connection. The server or care provider computing device 160 may communicate the updated treatment protocol to be received by the electronic computing device 120.

In one example, the updated treatment protocol may be determined by any combination of care provider input, whether human or programmed rules, patient input from the patient interface 130, data from the sensors 140, 142, 144, EMR data, and data regarding the treatment itself.

During another point of operation, the electronic computing device 120 may be configured to communicate the updated treatment protocol to the medical device 110 to enable an updated treatment of the patient. When the medical device 110 is next operated, the updated treatment protocol may determine what treatment is provided or allowed. In one example, this may occur at least partly through the administration of a treatment session. For instance, an updated treatment protocol may be determined and communicated to the medical device 110 halfway through a treatment session such that the second half of the treatment session is different from the first half. In another example, the updated treatment protocol may be determined after the completion of one treatment session and may be enacted during a second treatment session. The updated treatment protocol may be determined at any time before, during, or after treatment, and may be enacted at any time after being determined.

Figure 2:
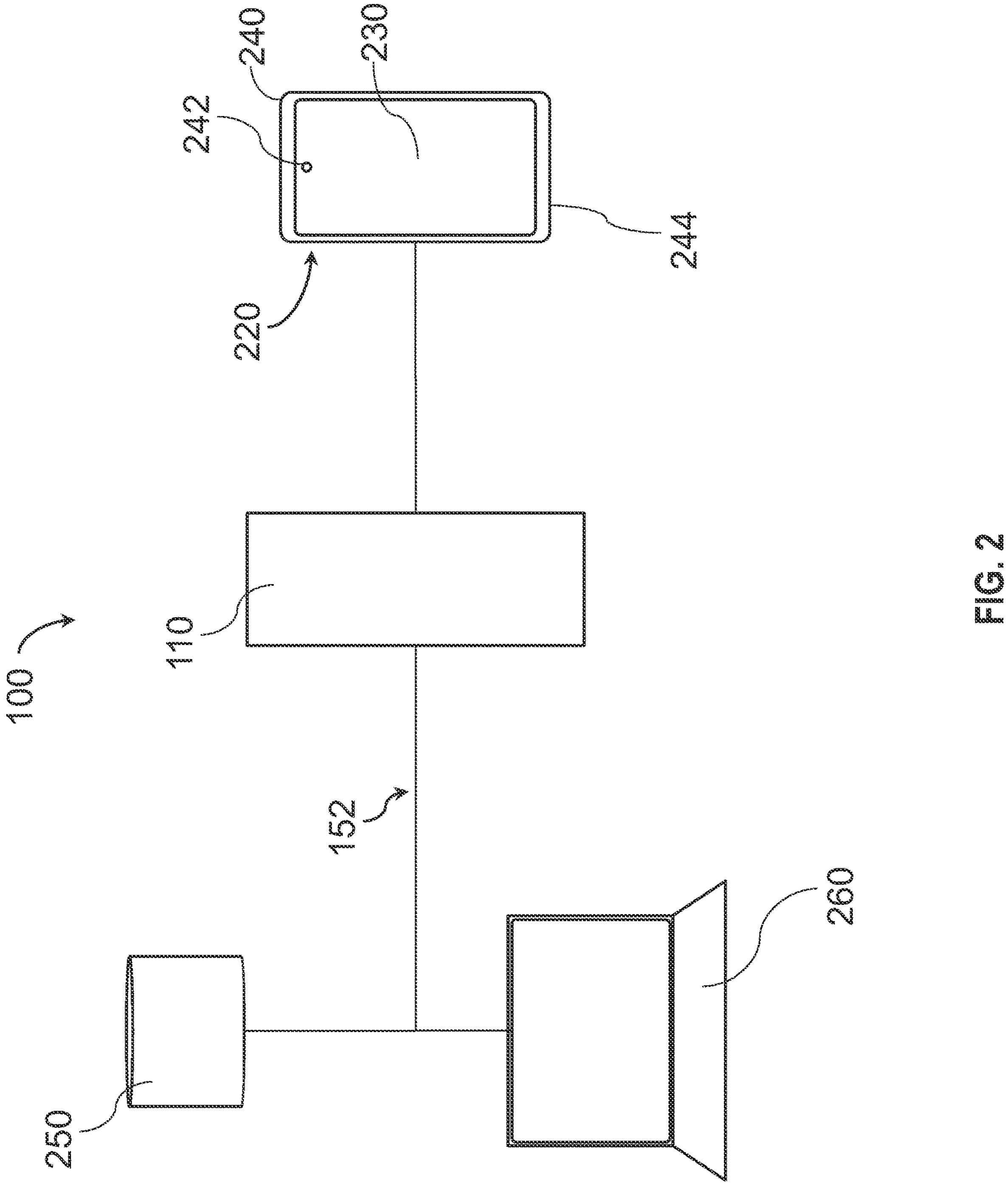
FIG. 2 is a diagrammatic illustration of the system of FIG. 1 in operation with a mobile device, in accordance with the first exemplary embodiment of the present disclosure.

FIG. 2 is a diagrammatic illustration of the system 100 of FIG. 1 in operation with a mobile device 220, in accordance with the first exemplary embodiment of the present disclosure. The system 100 shown in FIG. 2 is provided to illustrate a particular embodiment of the present disclosure, and should be understood to be exemplary in nature. FIG. 2 may be understood with reference to FIG. 1.

As shown in FIG. 2, a medical device 110 is in communication with a mobile device 220, which may be the electronic computing device 120 described relative to FIG. 1. The mobile device 220 may include a screen 230 displaying a graphical user interface and allowing tactile input from the patient. A plurality of sensors, including a rear camera 240, front camera 242, and microphone 244 may be included on the mobile device 220. The mobile device 220 and the medical device 110 may be in communication over a network connection 152 with a cloud server 250 and a provider electronic device 260. In operation, the mobile device 220 may be configured to: receive an initial electronic treatment protocol from the cloud server 250, communicate the initial electronic treatment protocol to the medical device 110 to enable an initial treatment of the patient; receive patient input through the screen 230 and the sensors 240, 242, 244; receive an updated treatment protocol based on the patient input; and communicate the updated treatment protocol to the medical device 110 to enable an updated treatment of the patient.

In the example shown in FIG. 2, the rear camera 240 may be used to measure the patient's pulse rate from time to time, while the front camera 242 and microphone 244 may be used to provide a video stream of the patient and/or the medical device 110 to the server 250 or the care provider electronic device 260. The video stream may allow a care provider to observe the patient or the medical device 110 while in operation, and may allow the care provider to make determinations about the effectiveness of the treatment session as it is occurring. In one example, a software program running on the server 250 may analyze the visual and/or audio data from the stream to determine whether the treatment is effective. For instance, in an example where the medical device 110 is a dermatological device, the video stream may indicate whether the patient's skin is responding well to the treatment by showing redness, swelling, clarity, and the like. In an example where the medical device is a home COVID test, the video stream may indicate whether the patient has correctly followed the testing procedures. In one example, the sensor data may be analyzed by computer algorithms such as machine learning algorithms, neural networks, computer vision algorithms, and the like.

In the example shown in FIG. 2, the patient may receive a round of treatment, or a portion of a round of treatment, and may be prompted to answer one or more questions regarding the treatment, the patient's mental state, and the like. For instance, in an example where the patient is being treated for depression with a transcranial magnetic stimulation device, the questions may include a standard or medically-accepted depression test to score the patient's depression. Results from before the administered treatment may be compared with results after the administered treatment in order to determine the efficacy of the administered treatment. The prompted questions may be delivered textually or audially by an application running on the mobile device 220, or by a care provider communicating over a video or audio stream.

Figure 3:
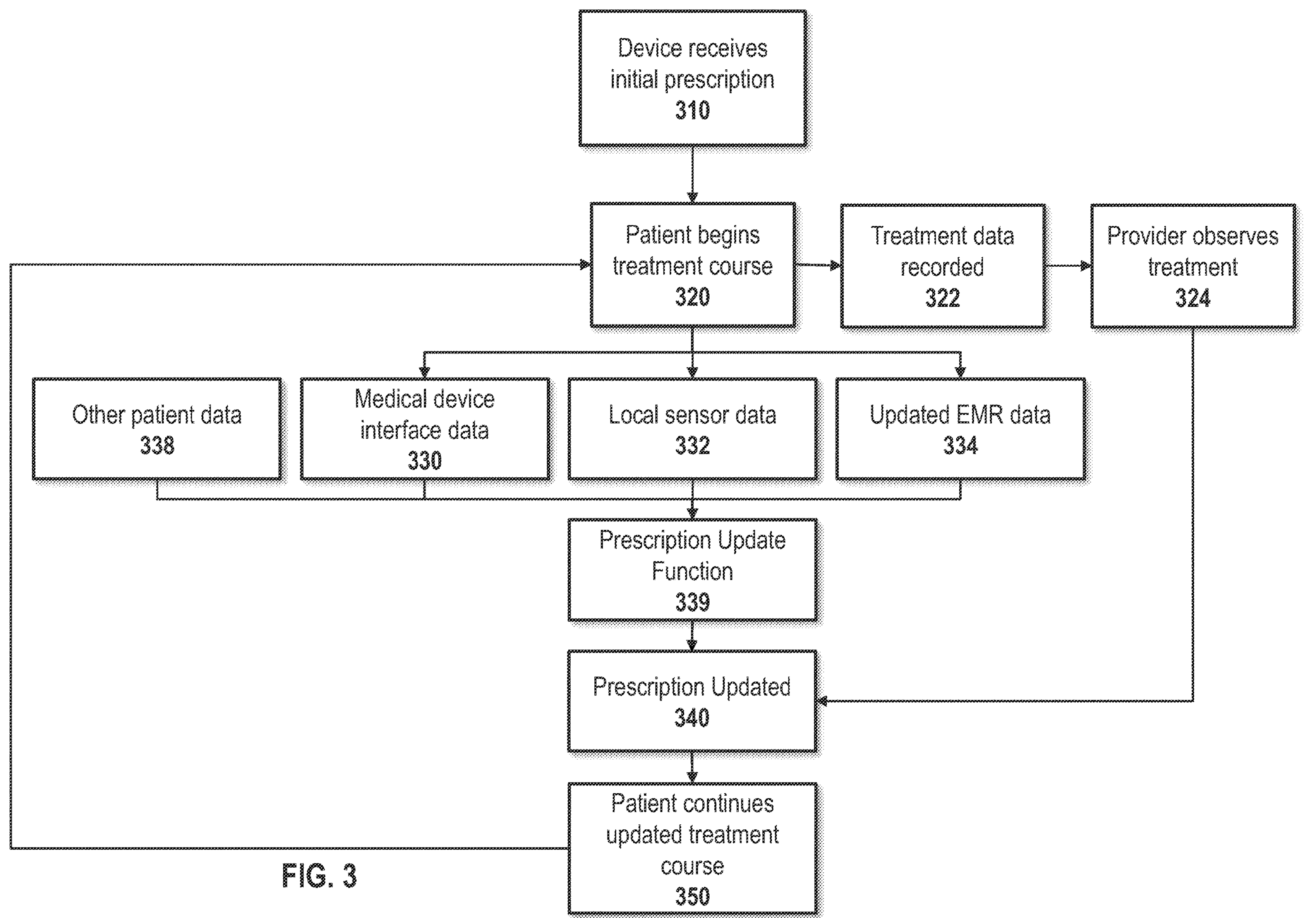
FIG. 3 is a flowchart illustrating the operating process of the system of FIG. 1, in accordance with the first exemplary embodiment of the present disclosure.

FIG. 3 is a flowchart 300 illustrating the operating process of the system of FIG. 1, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

The operating process described by FIG. 3 may be understood in relation to a treatment protocol or treatment course or prescription, observation, and modification of a treatment course as is usually made between a patient and a care provider in in-person settings. These steps, as described below relative to the remote administration of treatment, may further be rendered into steps understood and executed by the electronic computing device 120 and medical device 110 of FIGS. 1-2, above.

In step 310, the medical device may receive an initial prescription for treatment. This initial prescription may indicate any of several parameters for treatment, including the number of doses, frequency, total duration, number of treatment sessions, time period over which treatment is to be provided, and the like. The initial prescription may be communicated by a care provider to the medical device, for instance, by way of the Internet and through an electronic computing device.

In one example, prior to receiving treatment, the patient may be assessed for treatment by one or more methods, including in-person assessments, remote video or audio assessments, paper or electronic written assessments, biometric screenings, laboratory panels, and the like. A provider, care provider software, or care provider entity may determine whether the patient should receive treatment based on these prior assessments, and may further determine the nature and degree of treatment to be administered. This may form the basis for the initial prescription and treatment plan pursued.

The initial prescription may take any suitable digital, electronic, or analog form. In one example, the initial prescription may be communicated in a readable or scannable coded form, such as a bar code, QR code, and the like. For instance, a QR code may be readable by a user's electronic computing device 120, by the medical device 110, or by the care provider computing device 160. The QR code may be unique to each prescription via a standard lookup table or may be encoded according to a particular protocol. Each aspect of the QR code may define some parameter of the initial prescription, including the prescriber, patient, number of authorized sessions, and particular information about the treatment, as is discussed further relative to FIG. 5, below. The care provider may generate an updated QR code or other form of prescription notation corresponding to changes or updates in the prescription as is described further herein.

In step 320, the patient may begin the treatment course. In one example, the patient may perform setup, startup, and positioning operations for the medical device. During setup, the patient may follow instructions communicated by the medical device or the electronic computing device to ensure that the devices are powered on, calibrated, connected to a network connection, and the like. During startup, the patient may follow instructions communicated by the medical device or the electronic computing device to ensure that the devices have accessed the network connection, retrieved the initial prescription, and loaded the instructions for execution by the medical device. During positioning, the patient may follow instructions communicated by the medical device or the electronic computing device to ensure that the medical device is properly positioned, oriented, or otherwise configured to deliver treatment. In one example, all of these instructions may be communicated by an electronic computing device such as the patient's mobile device. The mobile device may provide visual, auditory, and/or tactile instructions by way of a software application or a web page accessed over the network connection. In another example, at least a portion of the instructions may be communicated by a care provider or may be observed by the care provider so that the care provider can ensure the medical device is ready to provide treatment. The observation may be remote by way of cameras and microphones on the patient's mobile device.

Once the medical device is ready to provide treatment, the treatment may be administered. In one example, the patient may control the onset of the treatment. In another example, the care provider or software within the medical device, electronic computing device, the server, or the care provider computing device may control the onset of the treatment. In another example, the medical device may only be allowed to proceed with treatment if the medical device or the electronic computing device has confirmed that an initial prescription has been received and loaded. In one particular example, a care provider using a provider computing device may control the onset of treatment by delivering an initial portion of the treatment, to make certain that all is proceeding well, then delegate control of the treatment to the patient or to another user. In another example, an electronic user such as an artificial intelligence, bot, or other software program may control the onset of treatment. The electronic user may determine, based on the initial prescription, how to begin delivery of the treatment, and may adjust the treatment during the course of treatment as described below. As used herein, "control" means to dictate the onset or cessation of an entire treatment protocol (i.e., to begin or conclude a session) as well as to dictate the application of particular treatment aspects (i.e., starting and stopping the delivery of individual pulses during a TMS treatment).

In step 322, treatment data may be recorded while the treatment is being administered. In one example, patient input may be requested and/or received during treatment, and this input may be recorded. Patient input may include such information as the patient's perception of the treatment, whether the patient is experiencing pain or discomfort, whether the location, intensity, or frequency of the medical device operation should be changed, and the like. In one example, patient data may be gathered, received, and transmitted by the sensors operating in concert with the medical device and the electronic computing device. Sensor data gathered may include information about the patient's condition, such as pulse rate, oxygen levels, blood composition, and the like. Sensor data may also include information about the ambient environment when appropriate. In one example, all of this data may be communicated over the communications network to the server or the care provider computing device.

In step 324, in one example, the care provider may observe the treatment as it is in progress. For instance, the care provider may monitor video, audio, and patient sensor data while the treatment is administered. In another example, a software application running on the care provider side may monitor one or more sources of data to identify concerns or anomalies that might require the treatment to cease. The software application may communicate an alert to the care provider and/or the patient in the form of a visual, audio, or tactile alert in such an event.

In steps 330-338, other patient data, medical device interface data, local sensor data, and updated EMR data, respectively, may be analyzed along with the initial prescription to determine whether adjustments to the prescription are required. This analysis and adjustment may occur at any time during the administration of the prescription, such that an updated prescription is at least partially dependent on the data received in steps 330-338. In one example, the data received in steps 330-338 may be subject to a mathematical operation on a set of variables compared against a set of reference values to determine a prescription output calculation. For instance, a patient may initially receive a treatment of 50 doses of a therapeutic, and may subsequently provide data through the patient interface regarding the patient's condition. The patient data may be weighted, modified, normalized, or otherwise processed to make it suitable to use in a scoring method. If the data indicates that the patient's condition remains below or above a threshold value as determined by the scoring method, the prescription may be updated to deliver an additional 20 doses of the therapeutic. If the data indicates that the patient's condition has achieved the threshold value, the prescription may be updated to discontinue any further treatment.

In step 330, the patient may provide data through the patient interface. This may include answering questions or prompts, performing on diagnostic tests, free-form input, and the like. In general, patient interface data may be self-reported data entered through the electronic computing device. In step 332, local sensors may provide data to the electronic computing device. This may include visual and audio data, as well as patient biological data obtained from sensors such as electroencephalograms, heart rate monitors, blood glucose sensors, thermometers, and the like. In step 334, the patient's EMR may be consulted to determine whether there have been any updates to the patient's medical history that might be relevant. EMR data may be accessed through one or more cloud servers over at least one network connection. In step 338, the data from other patients in the system may provide data to the electronic computing device for the purpose of updating a single patient's data. This may include their history of medical device interface data, local sensor data, electronic medial records data.

As applied to a trial, the same prescription may be written for multiple patients in a trial. Information gained from others in the trial, e.g., information on how other patients in the trial improve (e.g. lower doses are yielding better improvements in depression scores) and then our patent claim here is that these learnings could be propagated through this adaptive prescription concept to benefit the patient or trial design. As an example, the prescription can include a field indicating whether a patient is in the active treatment group or the placebo group. This assignment is flexible and can change during the trial. For instance, in a trial with 10 patients in the active group and 4 in the placebo group, the group assignment for some patients may be altered. Changing the assignment of 3 patients from the active group to the placebo group would balance the numbers, resulting in 7 patients in each group. This automatic prescription adjustment based on the values of other related prescriptions helps maintain the trial's integrity and ensures a more balanced and effective study.

The prescription may be updated according to any logical rules and any accepted medical practices. For instance, the updated prescription may include additional treatment until the patient's assessed scores reach or surpass some threshold value, as above. This additional treatment may include constant values, e.g., 10 additional treatments until the threshold is met, or may be conditional upon the difference between the patient's scores and the threshold value, e.g., 10 additional treatments if the difference is 10 points, but 5 additional treatments if the difference is within 5 points. The updated prescription may be stepped, linear, quadratic, logarithmic, or follow any suitable distribution equations. The updated prescription may include conditional logic, nested logic, and loops. The updated prescription may self-reference the behavioral usage of the prescription in order to determine subsequent treatments. The updated prescription may reference time. The updated prescription may include multiple treatments or output values.

The following operating examples are illustrative of possible updated prescriptions in the context of transcranial magnetic stimulation (TMS) of a human patient:

Example 1—The patient will receive 50 doses of TMS unless the mean depression score during treatment, as reported by the patient in response to a standardized questionnaire, remains above 100. If the mean depression score remains above 100, the medical device may deliver an additional 20 doses of TMS.

Example 2—The patient will receive 50 doses of TMS unless the mean depression score during treatment, as reported by the patient, remains above 100. If the mean depression score remains above 100, the medical device may deliver an additional 20 doses of TMS. If the score is above 75, the medical device may only receive an additional 10 doses of TMS.

Example 3—The patient will receive 50 doses of TMS unless the mean depression score during treatment, as reported by the patient, remains above 100. If the mean depression score remains above 100, the medical device may deliver an additional 20 doses of TMS. After the additional doses have been completed, if the mean depression score remains above 90 the medical device may deliver an additional 15 doses of TMS.

Example 4—After the patient completes 50 doses of TMS, the patient may receive 1 dose of TMS for every 5 points above 100 their depression score totals.

Example 5—The patient will receive 50 doses of TMS. If the patient takes 1 dose per day without missing any days, the patient will receive 10 additional doses of TMS.

Example 6—The patient will receive 5 doses of TMS per day for 10 days, and then 1 dose per day after that.

Example 7—The patient will receive 50 doses of TMS, and if the patient has a depression score over 100 and does not miss any days, the patient will receive 10 additional doses of TMS.

Example 8—The patient will receive 50 doses of TMS at 10 Hz, and if the patient has a depression score over 100, the patient will receive 10 additional doses of TMS at 1 Hz.

More broadly, the updated prescription may follow any suitable algorithmic expression in step 339, as determined from analysis of the prevailing medical practices, the patient interface data, the local sensor data, and the updated EMR data.

In step 340, the prescription may be updated. This may include the digital prescription file, and it may include communication of the updated prescription to the electronic computing device and the medical device. The updated prescription may be made at any time before, during, or after a treatment session is administered.

In one example, the updated prescription may be viewable by the patient on the electronic computing device through the patient interface. For instance, the patient may see a notification on their mobile device indicating that an updated prescription has been issued, and may open the notification to view the update to the prescription. The notification may be any suitable type and number of notifications, including text message, email, push notification, audio, tactile, or other types of visual notifications.

In another example, the patient interface may display graphical information indicating how the patient is progressing through treatment. In one instance, the display may show a percentage of the entire treatment course that has been completed or a number of sessions completed out of the total. The display may also show a visual indication of which step or variation in treatment the updated prescription is requiring. These may all serve to help the patient understand the treatment being provided.

In another example, the prescription may be updated according to data obtained by a sensor such as an EEG, EKG, or EMG in step 332. For instance, during the course of treatment, the patient may simultaneously undergo monitoring by EEG, EKG, or EMG. Based on the information obtained through the monitoring tests, the initial prescription may be adjusted to optimize the treatment's efficacy. In one instance, this data may be supplemented by images from a camera to confirm results. In another instance, the updated prescription may be made according to an algorithm, as described above. In another instance, the updated prescription may be made by a care provider based on the care provider's medical opinion.

In step 350, the patient may continue with the updated treatment course. In operation, the patient may use the electronic computing device to update the treatment by downloading the most current treatment course. In one example, the electronic computing device may automatically check for updated prescriptions upon startup, or before administering treatment. In another example, the patient may confirm the updated prescription before operating the medical device. In another example, the care provider may be required to download or confirm the updated prescription to the electronic computing device before the medical device is allowed to perform the treatment.

The initial prescription may be edited, paused, resumed, or canceled by a care provider with sufficient privileges. Any changes may be performed in-person or remotely using a web or app interface. In one example, changes made according to step 340 on a local device, such as a care provider computing device 160, may be pushed over the network 152 to the server 150, the medical device 110, and/or the user electronic computing device 120. In another example, changes to the prescription may be made on a remote server 150 from a remote care provider computing device 160 and pulled to the user's electronic computing device 120.

Figure 4:
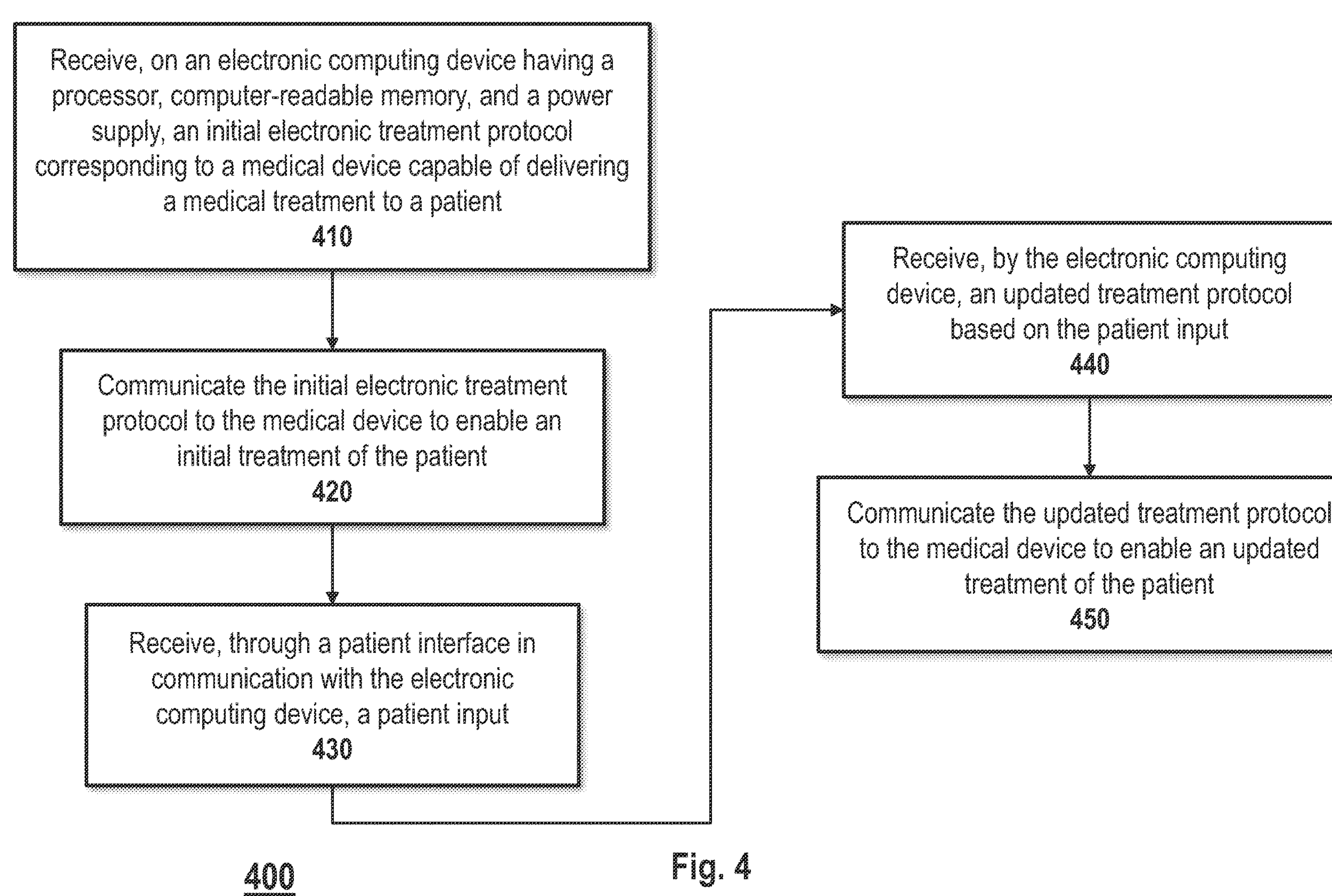
FIG. 4 is a flowchart illustrating a method of administering remote treatment with a medical device, in accordance with the first exemplary embodiment of the present disclosure.

FIG. 4 is a flowchart 400 illustrating a method of administering remote treatment with a medical device, in accordance with the first exemplary embodiment of the present disclosure. The method may further include any other features, components, or functions disclosed relative to any other figure of this disclosure.

Step 410 includes receiving, on an electronic computing device having a processor, computer-readable memory, and a power supply, an initial electronic treatment protocol corresponding to a medical device capable of delivering a medical treatment to a patient.

Step 420 includes communicating the initial electronic treatment protocol to the medical device to enable an initial treatment of the patient.

Step 430 includes receiving, through a patient interface in communication with the electronic computing device, a patient input.

Step 440 includes receiving, by the electronic computing device, an updated treatment protocol based on the patient input.

Step 450 includes communicating the updated treatment protocol to the medical device to enable an updated treatment of the patient.

Figure 5:
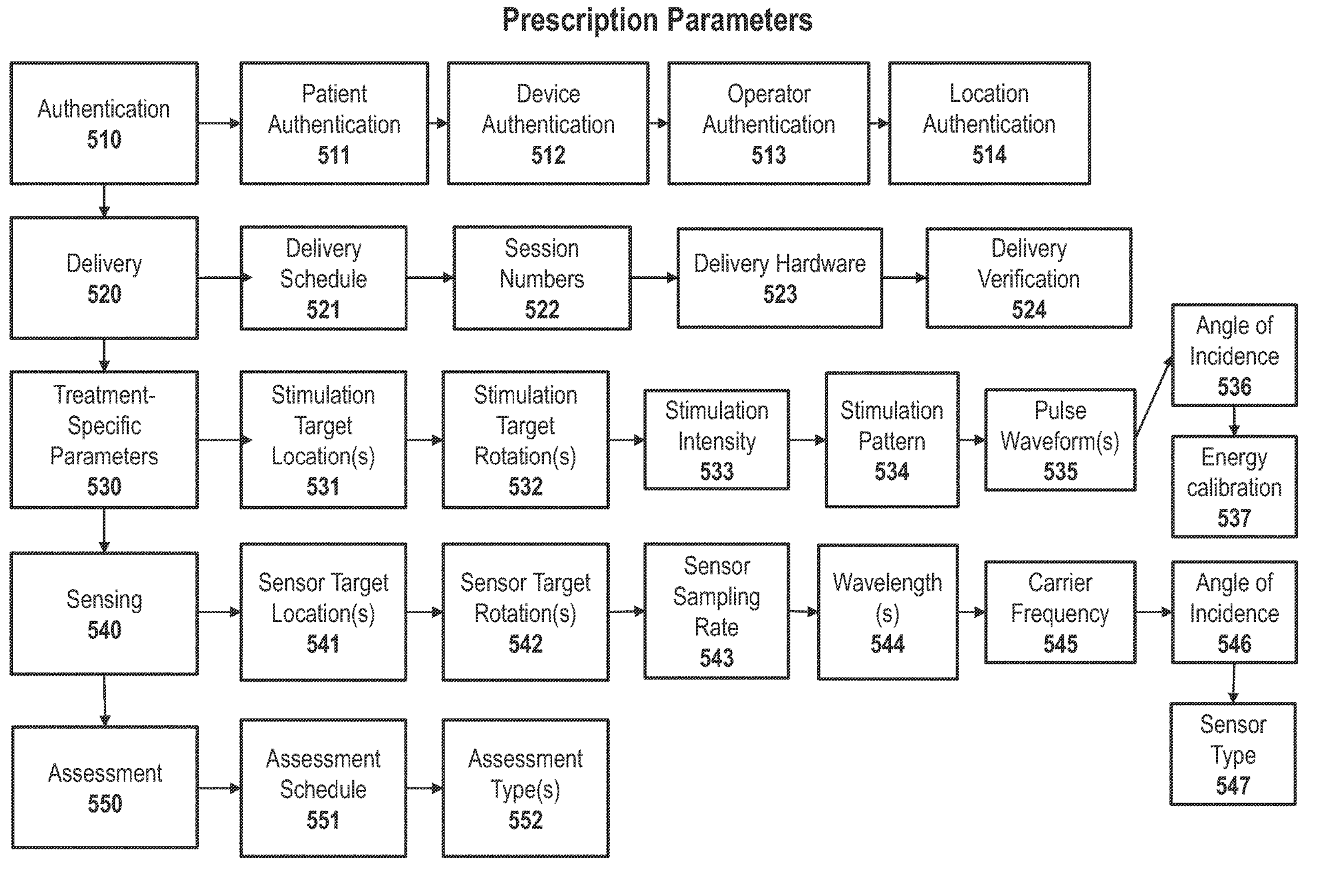
FIG. 5 is a flowchart illustrating exemplary prescription parameters implemented by the system of FIG. 1, in accordance with the first exemplary embodiment of the present disclosure.

FIG. 5 is a flowchart 500 illustrating exemplary prescription parameters implemented by the system 100 of FIG. 1, in accordance with the first exemplary embodiment of the present disclosure. The prescription parameters may include one or more conditions which are ascribed to the prescription and must be met for the treatment to be successfully delivered. In a typical prescription known in the art—which is a type of treatment protocol—this might include conditions such as a dosage, frequency, and duration of treatment, e.g., a patient must take two pills per day for one week. Concerning the system for administering remote treatment with a medical device 110, such parameters may additionally include conditions related to the devices delivering the treatment, the persons receiving and providing the treatment, the timing and geographical location of the treatment, and several factors related to the treatment itself.

In contrast to traditional prescriptions that might specify a simple, fixed regimen (e.g., two pills per day for one week), the parameters in this system can be vectors that vary over time or treatment number. For instance, the dosage may change each day (1 pill on day 1, 2 on day 2, etc.), and these dosages can be further organized into nested vectors, accounting for different courses of treatment (first course: [1 2 3 2], second course: [2 3 2 3], and so forth). Thus together, the dosing parameter might be [[1 2 3 2], [2 3 2 3], [3 2 1]]. This allows for a nuanced approach that can potentially improve treatment efficacy by utilizing the precision capabilities of medical devices.

Additional parameters may be considered within the scope of this disclosure. The flowchart 500 illustrated herein is exemplary and is not intended to be limiting.

Any of the steps 510-537 may be performed, at least in part, electronically by one or more computing devices. For example, the electronic computing device 120, medical device 110, or care provider computing device 160 shown in FIG. 1 may perform any or any portion of the steps 510-537, alone or in concert with one another, in order to validate all of the conditions required by the prescription parameters. The hardware components relative to each device 120, 110, 160, discussed with respect to FIG. 1 above, may be used to perform certain of the steps as would be understood by one of skill in the art and will be explained in greater detail below. The computing devices 110, 120, 160 may operate across the network connection 152 to transmit, receive, process, and validate the data received by each device 110, 120, 160, and may further work in connection with the server 150. In one example, the hardware devices 110, 120, 160 may read, scan, decode, or otherwise interpret prescription instructions given by the care provider, which may be in electronic form as described above.

Step 510 illustrates an authentication process wherein the system 100 may determine that one or more conditions is aligned with what is required by the terms of the prescription. For instance, step 511 includes authenticating that the patient receiving treatment is the person authorized to receive treatment under the prescription. This authentication may be performed by any suitable process, including validating login credentials, validating physical identification documents such as a driver's license or ID card, validating biometric data such as retina, facial, fingerprint, or voice data, or through any combination thereof. An electronic computing device, such as the user electronic computing device 120, may be used to perform any of these processes. For example, a mobile device 220 may allow a user to enter login credentials such as a username, password, or birthdate, as well as biometric data such as a photograph or a fingerprint scan, any of which may be compared against a database, either local to the device or remote, to determine whether the user is the correct patient.

Step 512 includes authenticating a medical device delivering treatment. This may include electronically determining an identifier or other credential of the medical device, such as a serial number, MAC address, and the like, and comparing it against a database of devices permitted to provide treatment.

Step 513 includes authenticating the operator of the treatment, i.e., the medical care provider who is controlling or supervising any portion of the treatment. Authenticating the operator may be accomplished using any of the same methods described relative to step 511, above, and may be performed at least in part using the care provider computing device 160. For example, the medical care provider may enter login credentials, scan an ID badge, enter biometric data, or the like in order to verify their identity to administer the treatment.

Step 514 includes authenticating the location at which the treatment is being performed. This may include determining where the user, the user electronic computing device 120, and/or the medical device 110 are geographically located using GPS, Wi-Fi, or other verification methods. In one example, the system 100 may check that the user is at an authorized location, such as a medical facility, a nursing home, or a residence. In another example, the system 100 may check that the user is not attempting to receive treatment where doing so would put the user at risk of exposing sensitive medical information (i.e., in a public place) or at risk of danger (i.e., while driving, operating machinery, supervising children, etc.). In this manner, the system 100 may determine either that the user is at an authorized location or that the user is not at a prohibited location. The user may be asked, via the patient interface 130 to confirm their location and/or to confirm that they are not engaged in dangerous activities or in public spaces before proceeding with treatment.

Step 520 illustrates a process for verifying the parameters related to the delivery of the treatment. For instance, step 521 includes verifying the treatment schedule, which may include information related to the date, day of the week, time of day, length, timing of the treatment, or other factors. One or more of the electronic computing devices 110, 120, 160 may verify that treatment is being provided according to the prescribed schedule. In one example, this may include determining the prescription regimen, i.e., the number of times the treatment may be given over a period of time such as an hour, day, week, or month. The system 100 may read or determine a maximum number of treatments over each, every, or all periods. The system 100 may read or determine from the prescription a minimum interval between which treatments are allowed. The system 100 may read or determine a schedule, i.e., particular times at which delivery of treatment is prescribed and/or allowed. For instance, the care provider may order treatment between particular hours on a particular date and again on those same hours the next date. In scenarios where treatment parameters have a vector-like nature, each individual session's delivery schedule could be uniquely defined (thus, represented as a vector). For a patient undergoing multiple treatment courses, there would be a vector for each course, with each element of this vector representing the treatment schedule for each session within that particular course.

Step 522 includes reading or verifying the number of authorized treatment sessions. This may include the total number of sessions prescribed by the care provider and the number of sessions remaining. This data may be read or determined from the prescription.

Step 523 includes verifying that any hardware involved in providing the treatment is appropriate for providing that treatment. In one example, this may include verifying that the medical device 110 is not only authorized to access the treatment protocol, but is a device with appropriate capabilities or features. For instance, several medical devices in a product line may be capable of providing a basic treatment, but only certain devices may provide upgraded features. In another example, this may include verifying that any hardware in connection with the treatment protocol is powered on, operating nominally, connected to any networks 152, and the like. In one particular example involving TMS treatments, the system 100 may determine whether the connected hardware includes a suitable TMS pulse generator for delivering the prescribed treatment and/or a suitable TMS coil for delivering the prescribed treatment. Since there are numerous types of TMS pulse generators and TMS coils, the system 100 may compare an electronic report of the make and model number of each component against a database of suitable hardware components for the prescribed treatment protocol. The hardware parameter may also cover 'sham' hardware, used to simulate treatment in controlled trials without delivering actual therapy.

Step 524, labeled as 'Delivery Verification', is focused on ensuring that the specific parameters outlined in Steps 530 to 537 are accurately met before proceeding with treatment. This step involves a series of checks to confirm that conditions like the correct positioning of the device at the intended stimulation target location are achieved. Depending on the scenario, the nature of these checks can vary. In the simplest scenario, no additional validation may be required. However, in other cases, it might be necessary to get approval from a healthcare provider different from the one currently operating the device. Alternatively, an algorithm within the electronic computing device might be employed to carry out this verification process. For instance, an optical character recognition (OCR) algorithm could analyze a camera feed from the medical device to identify specific text that confirms the device is correctly positioned over the intended target location, thereby validating that parameter.

Step 530 illustrates a process for verifying and carrying out parameters that are specific to the prescribed treatment. Whereas the process for authentication in step 510 may be relatively the same regardless of the nature and type of treatment contemplated, the parameters described relative to step 530 may be highly dependent on the particular treatment. The parameters illustrated in steps 531-537 are shown as exemplary parameters with respect to TMS treatment protocols, although others may be considered to be within the scope of this disclosure.

Step 531 includes reading the stimulation target location, which is the placement on the patient's body where the TMS treatment device must be positioned according to the prescription. This may include specific positions on the patient's head. Step 532 includes reading the stimulation target rotation, which is the angular orientation of the treatment device at the target location according to the prescription. Step 533 includes reading the stimulation intensity, which is the amount of output that the treatment device should apply to the patient according to the prescription. In the context of TMS, especially during the energy calibration process known as motor thresholding, the intensity is often variable rather than constant. This process involves deliberately varying the pulse intensities to find the required energy level for activating neural tissue, leading to the specification of intensity values as a vector or nested vectors, rather than a single constant. Step 534 includes reading the stimulation pattern, which is the timing and frequency of the stimulating pulses applied according to the prescription. Examples of pattern sub-parameters may include pulses per burst, inter-pulse intervals, bursts per train, inter-burst intervals, trains per sequence, and inter-train intervals. Step 535 includes reading the pulse waveform, which is the shape of the electrical pulse applied during the stimulation according to the prescription. Step 536 includes reading the angle of incidence, which is the angle of stimulation relative to the surface of the head during the stimulation according to the prescription. Step 537 includes reading the energy calibration method-a crucial part of neuromodulation, where it's used to ascertain the amount of energy needed to be delivered to neural tissue for therapeutic effectiveness. Prevalent energy calibration methods include motor thresholding and neurocardiac. Motor thresholding involves delivering pulses to the motor cortex to induce movements in the hands, feet, or other muscle systems. Neurocardiac, on the other hand, involves stimulating brain regions that connect to the heart, affecting heart rate. Although these are common methods, other approaches are also recognized in scientific literature. These energy calibration techniques are not only vital for setting the intensity of stimulation during treatment but also other parameters including the timing pattern of pulses and the total number of pulses in a therapy session. The system 100 may read any or all of these treatment-specific parameters from the prescription and may communicate them to the medical device 110, the user electronic computing device 120, and/or the care provider computing device 160.

Step 540 illustrates a process for verifying and implementing sensor data collection parameters as part of the prescribed treatment. This acknowledges that a prescription extends beyond treatment protocols and devices, also including sensor data collection from the patient to inform and optimize treatment protocols. For instance, a prescription might involve gamma knife radiation at a specific location, coupled with EEG data collection between treatments to adjust future treatment parameters. In this way, the sensing protocol is a part of the prescription as it must be done in order for the treatment to be delivered as intended by the prescriber. Akin to Step 530, Step 540 may be highly dependent on the particular sensing protocol. The parameters illustrated in steps 541-547 are shown as exemplary parameters with respect to neuroimaging sensing protocols, although others may be considered to be within the scope of this disclosure.

Step 541 includes placing the sensor targets in a particular location or locations. This might be a single location for MEG and multiple locations for EEG. Step 542 includes sensor target rotation(s) which indicate at what angles the sensors should be placed at with respect to the target location(s). Step 543 includes the data collection sampling rate of the sensor or sensors. Step 544 includes the wavelength(s) involved in some sensors like near infrared spectroscopy. Step 545 includes the carrier frequency involved in some sensors like near infrared spectroscopy. Step 546 includes the angle of incidence which is the normal vector of the scalp at the stimulation location with respect to the sensor. Step 547 includes the sensor type which specifies the type of sensor technology to be used—for example EEG vs NIRS—and even the subvariant of a technology like dry vs wet EEG electrodes.

Step 550 outlines a process for verifying and implementing patient assessment parameters as part of the prescribed treatment. This emphasizes that prescriptions also include patient assessments, which are crucial as they can influence treatment efficacy. The mechanism is that the assessment results can modify treatment parameters, making outcomes more effective. As an example, if a patient's depression score on a PHQ-9 scale is above value eight, the prescription's algorithm expression may unlock an additional ten sessions of treatment 522.

Step 551 includes specifying a temporal schedule for treatments, ranging from simple post-treatment assessments to more complex schedules, like daily assessments during treatment delivery. A more complex schedule might specify the patient take a PHQ-9 scale every day treatment is to be delivered, between 9 am and 10 am mountain time. Step 552 specifies the type of assessments to be taken, including the exact scale (e.g., PHQ-9, GAD-7) and who completes it, whether the patient, a care provider, or a collateral historian.

More broadly, a prescription in this context is a potential combination of authentication, delivery, treatment-specific, sensing, and assessment parameters. The corresponding data from these parameters can interact according to an algorithmic expression to update the treatment's current values in a closed-loop manner, all aimed at delivering optimal patient treatment.

Figure 6:
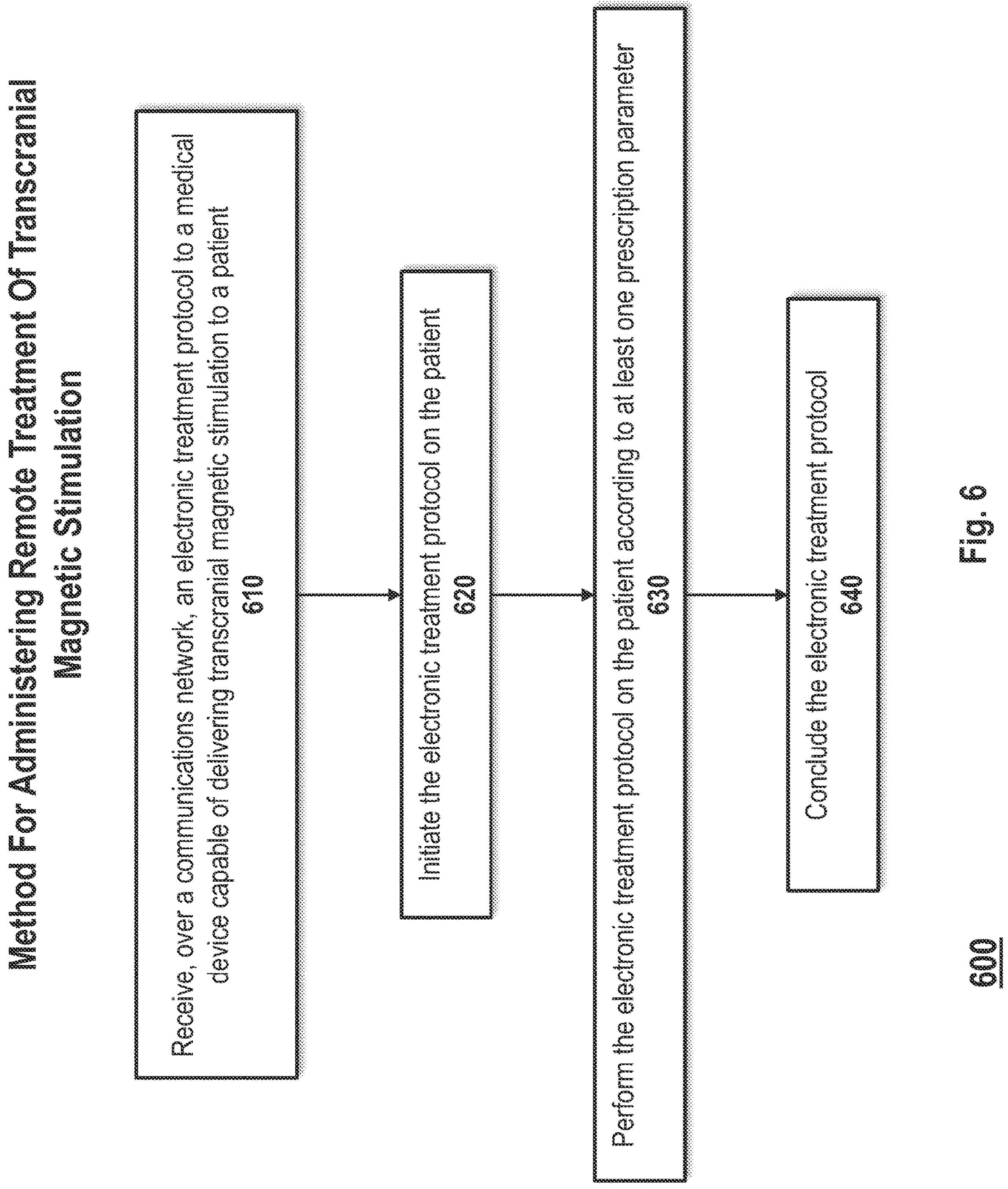
FIG. 6 is a flowchart illustrating a method for administering remote treatment of transcranial magnetic stimulation, in accordance with the first exemplary embodiment of the present disclosure.

FIG. 6 is a flowchart 600 illustrating a method for administering remote treatment of transcranial magnetic stimulation, in accordance with the first exemplary embodiment of the present disclosure. Step 610 includes receiving, over a communications network, an electronic treatment protocol to a medical device capable of delivering transcranial magnetic stimulation to a patient.

Step 620 includes initiating the electronic treatment protocol on the patient.

Step 630 includes performing the electronic treatment protocol on the patient according to at least one prescription parameter.

Step 640 includes concluding the electronic treatment protocol.

Figure 7:
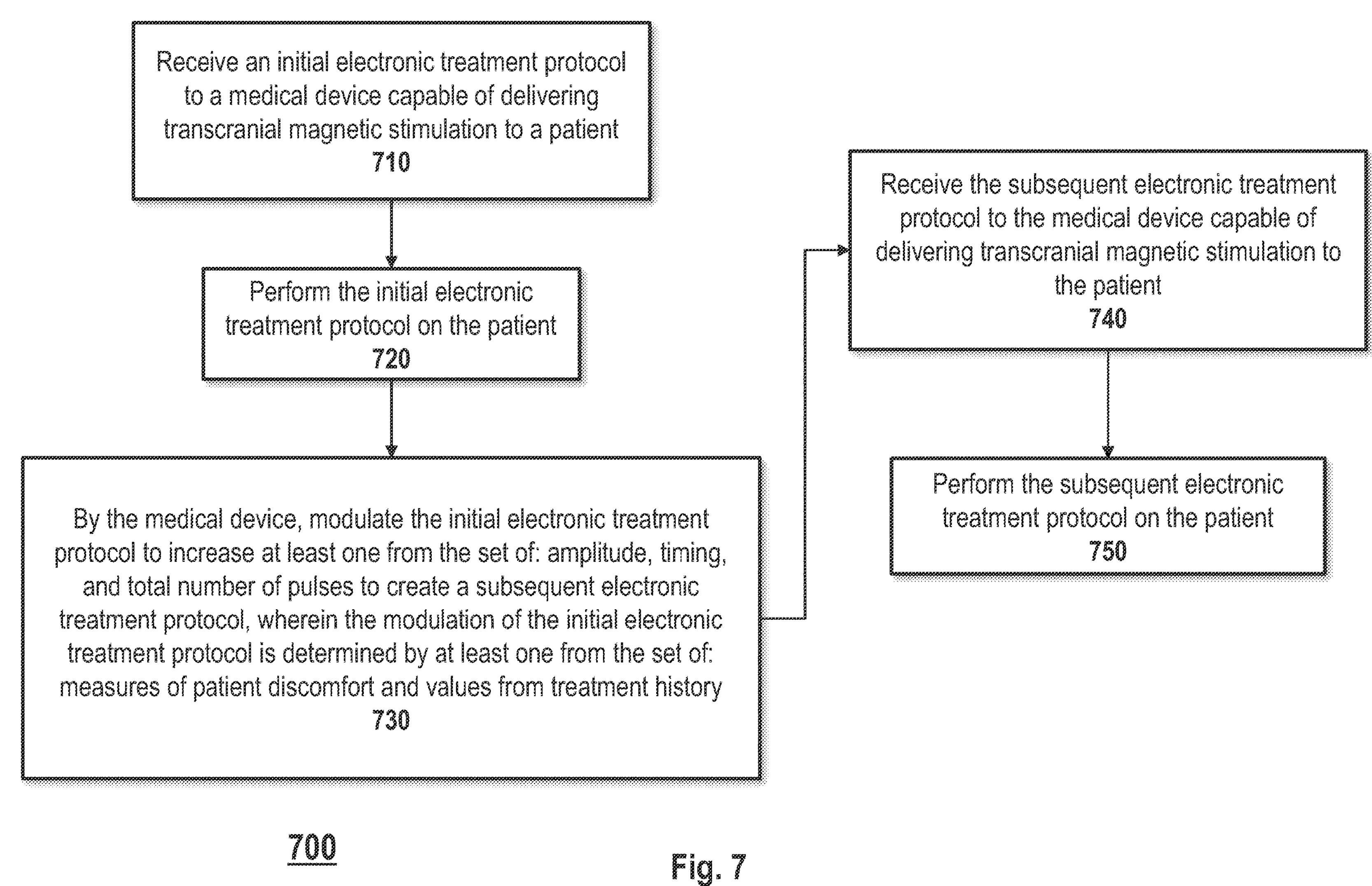
FIG. 7 is a flowchart illustrating a method for administering treatment of transcranial magnetic stimulation, in accordance with a second exemplary embodiment of the present disclosure.

FIG. 7 is a flowchart 700 illustrating a method for administering treatment of a human animal by transcranial magnetic stimulation, in accordance with a second exemplary embodiment of the present disclosure. The method of FIG. 7 may be understood and performed with reference to any of FIGS. 1-6, above. For example, the TMS devices described above may be used to perform the method of FIG. 7, as may any other suitable components, steps, processes, or procedures.

Step 710 includes receiving an initial electronic treatment protocol to a medical device capable of delivering transcranial magnetic stimulation to a patient. The initial electronic treatment protocol may be defined by one or more characteristics corresponding to TMS treatment procedures, including the pulse amplitude, pulse sequence timing, total number of pulses, and stimulation target, as described above. In particular, the initial electronic treatment protocol may be set at a lower boundary for effective treatment, with the patient's comfort or toleration of the treatment as a primary consideration in determining the treatment protocol. For example, characteristics such as the starting amplitude of the TMS pulses may be determined not by the intended therapeutic dosages, but by the amplitude or range of amplitudes which patients can comfortably tolerate. In one example, this may include very low initial amplitudes, while in another example, it may include initial amplitudes just below the therapeutic amplitude. In one example, the determination of which low starting amplitude to select may be made based on aggregated data from other patients. In another example, it may be made based on historical data from the current patient.

Step 720 includes performing the initial electronic treatment protocol on the patient. The initial electronic treatment protocol may be performed either by a care provider or a patient, in-person or remotely as described above. The frequency and duration of the treatment may be determined by the protocol.

Step 730 includes by the medical device, modulating the initial electronic treatment protocol to modify at least one from the set of: pulse amplitude, pulse sequence timing, total number of pulses, and stimulation target to create a subsequent electronic treatment protocol, wherein the modulation of the initial electronic treatment protocol is determined by at least one from the set of: measures of patient discomfort and values from treatment history. In this step, the TMS device may modulate the initial electronic treatment protocol in order to bring the treatment nearer to the desired therapeutic level as quickly as possible. For instance, the pulse amplitude, the timing of the pulses, or the total number of pulses delivered may be modified from the number indicated by the initial electronic treatment protocol toward a number that is therapeutically indicated to be effective. In one example, measures of patient discomfort may be considered when determining the size and scope of this modulation. Factors that may affect measures of patient discomfort are discussed in greater detail relative to FIG. 8, below. In another example, treatment history and historical treatment values may be considered when determining the size and scope of this modulation. Factors that may affect the treatment history are discussed in greater detail relative to FIG. 8, below. The TMS medical device may create an updated, subsequent electronic treatment protocol containing new, modified treatment parameters for the patient. These new, modified treatment parameters may be at least incrementally closer to a therapeutic dosage indicated for effective treatment while considering the patient's tolerance for the treatment.

Step 740 includes receiving the subsequent electronic treatment protocol to the medical device capable of delivering transcranial magnetic stimulation to the patient.

Step 750 includes performing the subsequent electronic treatment protocol on the patient. The subsequent electronic treatment protocol may be a treatment having a modified pulse amplitude, pulse sequence timing, total number of pulses delivered to the patient, and stimulation target. Provided the patient indicates a tolerance to the initial electronic treatment protocol, the subsequent electronic treatment protocol may be a further step toward full therapeutic levels of treatment.

In one example, steps 730-750 may be performed as an iterative process, whereby the treatment protocol is performed, modulated, updated, modulated, and performed again until the desired therapeutic dosage levels are reached. In one example, this process may be performed to reach a therapeutic dosage as quickly as possible in order to avoid wasting treatment time. Therefore, adjustments may be made in large increments according to the factors discussed. In another example, this process may be performed to ensure tolerability for a sensitive patient. Therefore, adjustments may be made in small increments. In another example, adjustments may be made on a variable scale-some large and some small, according to the factors discussed, and according to the goals of the treatment.

Figure 8:
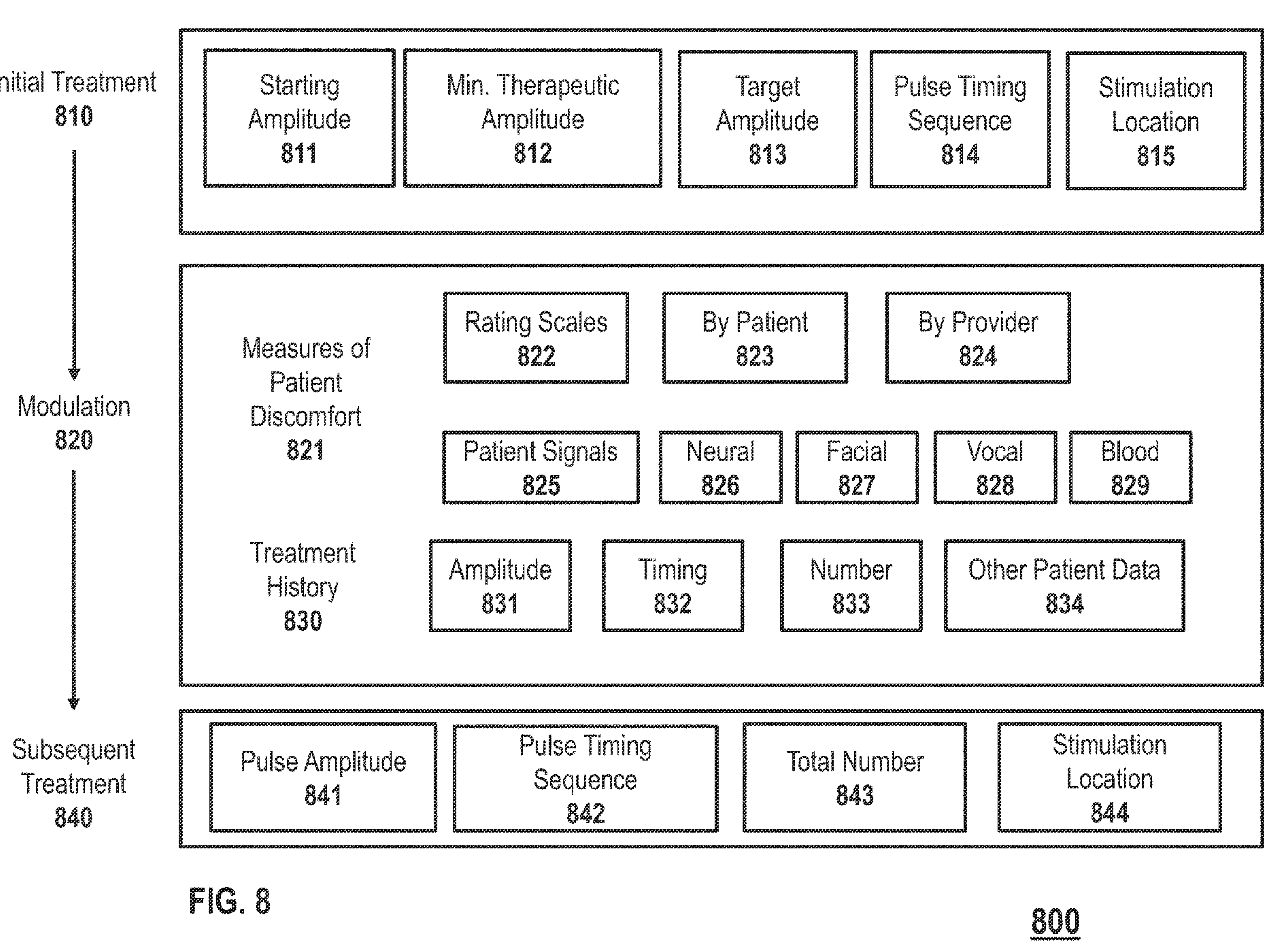
FIG. 8 is a flowchart illustrating an exemplary treatment protocol implemented by the method of FIG. 7, in accordance with the second exemplary embodiment of the present disclosure.

FIG. 8 is a flowchart 800 illustrating an exemplary treatment protocol for a human animal implemented by the method of FIG. 7, in accordance with the second exemplary embodiment of the present disclosure.

During the stage of initial treatment 810, the initial treatment protocol as described relative to FIG. 7 is followed. The initial treatment protocol may be determined by any suitable number and type of factors relevant to the treatment of medical conditions through the use of TMS treatment. Illustrated in FIG. 8 are exemplary factors including a starting amplitude 811, a minimum therapeutic amplitude 812, a target amplitude 813 pulse sequence timing 814—the exact timing of each pulse in a treatment—and stimulation location 815. As a consideration, a starting amplitude 811 may be a TMS pulse amplitude at which TMS pulses should initially be delivered. The minimum therapeutic amplitude 812 may be the smallest amplitude value for which a TMS pulse will deliver a therapeutic benefit. This may be lower than the ultimately-intended amplitude, but may still be an acceptable level of treatment at some early stages or sessions. The target amplitude 813 may include the value which is ultimately intended to be reached during treatment. The starting amplitude 811, minimum therapeutic amplitude 812, target amplitude 813, pulse sequence timing 814, and stimulation location 815 may all be considered together when setting the parameters of the initial treatment 810 in order to make the initial treatment 810 easy enough to be tolerated by the patient, but not so minimal that it will have no therapeutic effect. For instance, if the starting amplitude 811 is set far below the minimum therapeutic amplitude 812, it may require too many modulative iterations in order to reach a point where a therapeutic effect has been rendered. Likewise, if the target amplitude 813 is sufficiently far away from the starting 811, it may be impossible to reach the target amplitude 813 during the course of treatment, even with large modifications during the modulation period 820. Similarly, discomfort from TMS pulses varies widely across the head according to musculature, peripheral innervation, and thus the stimulation location 815 must similarly be known to assess the need for modifying the protocol.

During the stage of modulation 820, the initial treatment protocol may be modulated based on at least one from the set of: measures of patient discomfort 821 and values from treatment history 830. Measures of patient discomfort 821 may include objective and subjective measures indicated from the patient. In one example, these may include subjective rating scales 822, such as pain or discomfort assessments conducted by the patient 823 or by a care provider 824, or by any combination thereof. These assessments may include one or more questions directed toward the patient's condition during treatment in order to determine how the patient is tolerating the treatment. In one example, the patient may provide answers using a patient interface 130, such as a mobile device. In another example, the patient may answer questions orally with a care provider in-person. In another example, the care provider may provide answers using the care provider electronic device 260, or may receive answers orally, in-person.

Objective measures of patient discomfort 821 may include patient signals 825 indicated by one or more sensors gathering data from the patient during the initial treatment 810. The sensors may include any of the sensors 140, 142, 144 discussed previously herein and may measure neural activity 826, facial expressions 827, vocalizations 828, blood activity 829, and the like. Neural activity 826 may include baseline brain activity and changes caused by the onset of treatment, which may indicate pain or discomfort, or other more serious responses. Facial expressions 827 may include data from cameras and other visual sensors indicating unhappiness or other facial expressions showing discomfort, involuntary movements, increased perspiration, and the like. Vocalizations 828 may include audio data from microphones and the like indicating the patient is communicating pain, such as words, exclamations, increased breathing rate, and the like. Blood activity 829 may be data from blood pressure sensors, heart rate sensors and the like indicating that the patient is experiencing certain increases in blood pressure which would be indicative of discomfort. Other objective measures of patient discomfort 821 may be considered as well or in conjunction with these measures 825-829, which are offered as exemplary and are not intended to be limiting. In one example, the subjective and objective measures of patient discomfort 821 may all be considered together. Certain measures may be given more or less weight in the consideration.

Values from treatment history 830 may include the numerical values of the TMS pulses as treatment was previously performed. This may include the values for the pulse amplitude 831, timing of pulses 832, and number of pulses 833, as well as other relevant patient data. In one example, this treatment history data may be sourced from the patient receiving the treatment. In another example, the treatment history data may be sourced from one or more other patients who have received treatment. In this way, the TMS medical device may perform a modulation of the treatment based on a dataset of either or both the current patient and their response to previous treatments or a larger cohort of patients and their responses to previous treatments. This may allow the subsequent treatment to be developed based on modulations that have previously been successful considering the other factors—i.e., measures of patient discomfort 821, starting amplitude 811, minimum therapeutic amplitude 812, and target amplitude 813—at play during the initial treatment.

The initial treatment 810 may be modulated to change the values of the TMS pulses, thereby creating a subsequent treatment protocol 840. During the period of the subsequent treatment protocol 840, any one or combination of the values of pulse amplitude 841, pulse sequence timing 842, total number of pulses 843, and stimulation location 844 may have been modulated from the initial treatment protocol 810 to be closer to the target or desired values. In this way, the treatment may increase from a low-discomfort protocol to a more-effective, therapeutic protocol more quickly over the course of one or more iterations. These iterations may occur on a real-time basis-meaning the subsequent treatment protocol may be updated as frequently as every pulse.

The process of the modulation of the treatment at each iteration may be performed by a TMS medical device or by an electronic computing device 120. The TMS medical device or electronic computing device 120 may have a processor 122, memory 124, power supply 126, and other electronic components to allow the TMS medical device to analyze and interpret the measures of patient discomfort 821, treatment history 830, initial treatment 810 values, and other data together in order to determine a suitable subsequent treatment in the process.

Figure 9:
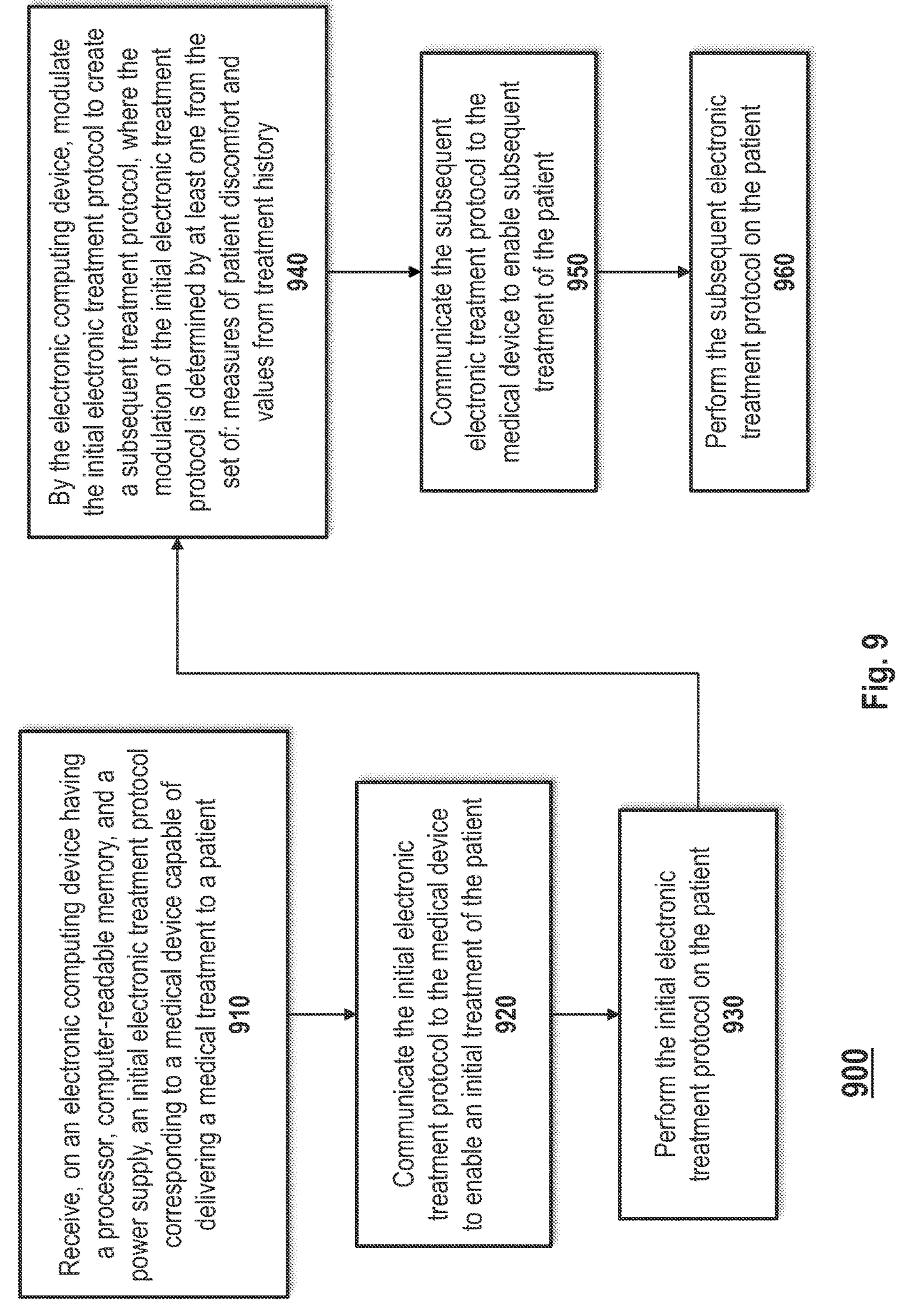
FIG. 9 is a flowchart illustrating a method for administering modulated treatment with a medical device, in accordance with the second exemplary embodiment of the present disclosure.

FIG. 9 is a flowchart 900 illustrating a method for administering modulated treatment of a human animal with a medical device, in accordance with the second exemplary embodiment of the present disclosure. The method of FIG. 9 may be understood with reference to FIGS. 1-8, above.

Step 910 includes receiving, on an electronic computing device having a processor, computer-readable memory, and a power supply, an initial electronic treatment protocol corresponding to a medical device capable of delivering a medical treatment to a patient. The electronic computing device may be the electronic computer device 120 shown in FIG. 1, above, and may include the same components discussed with reference therein. The initial electronic treatment protocol may be any treatment protocol as described above suitable for any medical device as described above. As discussed relative to FIG. 7, the initial electronic treatment protocol may be initially calibrated to provide a lower level of discomfort for the patient at the outset of treatment. For instance, a microneedling device may be calibrated to deliver shallow pricks, or fewer pricks per unit of time at the outset. An electrotherapy device may be calibrated to deliver a lower level signal. A laser skin treatment device may be calibrated to deliver a shorter pulse, or fewer pulses, or to deliver pulses over a smaller area at the outset.

Step 920 includes communicating the initial electronic treatment protocol to the medical device to enable an initial treatment of the patient. The initial electronic treatment protocol may be communicated the medical device in any of the ways described relative to FIG. 1. The medical device 110 may be configured to receive the initial electronic treatment protocol for implementation with the patient.

Step 930 includes performing the initial electronic treatment protocol on the patient.

Step 940 includes by the electronic computing device, modulating the initial electronic treatment protocol to create a subsequent treatment protocol, where the modulation of the initial electronic treatment protocol is determined by at least one from the set of: measures of patient discomfort and values from treatment history. With reference to FIGS. 1, 2, 7, and 8, the electronic computing device 120 may receive data from one or more sources, such as the patient interface 130, sensors 140, 142, 144, care provider computing device 160, or server 150. This data may indicate how the initial electronic treatment protocol has been proceeding with respect to the patient's comfort or tolerability as well as data to support the modulation of the initial electronic treatment protocol in the next iterative step. As is discussed with respect to FIGS. 7-8, measures of patient discomfort may be considered, including objective and subjective measures. This may include data gathered from the sensors 140, 142, 144, from the patient's vocal expressions, facial movements, increased heartrate, sweat levels, breathing, blood pressure, and the like, as well as patient responses to rating scales and survey questions. Measures of values from treatment history may be considered, including the number, intensity, timing, duration, and other characteristics of treatments which may be altered. The values from treatment history may be personal to the patient or may be aggregate of some group of patients. These historical values may be stored within the memory 124 of the electronic computing device 120 in the case of the personal patient data, in one example. In another example, historical values may be communicated through a server 150 over a communications network 152 to the electronic computing device 120.

The electronic computing device 110 may receive the data corresponding to the values from treatment history and the measures of patient discomfort, and, together with the initial electronic treatment protocol, may determine the patient's level of comfort with the initial round of treatment and may modulate the treatment to an increased level closer to a full therapeutic treatment level. The amount of this modulation may be large or small, depending on the factors described above, and may be greater in certain aspects of treatment, such as duration of treatment, than other aspects of treatment, such as intensity of treatment, or vice versa. The modulated treatment parameters may result in a subsequent electronic treatment protocol.

To clarify, any changes from the originally specified parameters in the initial treatment plan are considered as modifications to the treatment protocol in this context. If an algorithm adjusts factors like pulse amplitude, pulse sequence timing, the total number of pulses delivered to a patient, or the stimulation target, and these adjustments are based on the patient's discomfort or recorded treatment data and differ from the initial parameters, this process is viewed as creating an updated treatment protocol. Furthermore, if such data is constantly re-evaluated in real-time or near real-time, leading to changes in any of these parameters (pulse amplitude, pulse sequence timing, total number of pulses, and stimulation target), this process is regarded as a continuous update to the treatment protocol.

Step 950 includes communicating the subsequent electronic treatment protocol to the medical device to enable subsequent treatment of the patient.

Step 960 includes performing the subsequent electronic treatment protocol on the patient. Ideally, the patient will tolerate the subsequent electronic treatment protocol to a suitable degree. In one example, steps 940-960 may be performed iteratively, such that each subsequent electronic treatment protocol is performed, modulated, performed, and modulated again, until the treatment protocol has reached a desired suitable therapeutic level to effectuate a desired treatment, and the patient is tolerating the treatment well. If the patient appears to become uncomfortable during any iteration or to lose tolerance for any subsequent iteration of the treatment protocol, the electronic computing device may modulate the treatment parameters lower in certain cases in order to accommodate the patient or to continue the treatment as may be appropriate.

With reference to FIGS. 1-9, the subject disclosure can also be understood to describe a system for administering modulated treatment with a medical device. The system may include any of the components illustrated within the referenced figures, including a medical device 110 capable of delivering a medical treatment to a patient, an electronic computing device 120 having a processor 122, computer-readable memory 124, and a power supply 126. The electronic computing device 120 is in communication with the medical device 110, wherein the electronic computing device 120 is configured to: receive an initial electronic treatment protocol; communicate the initial electronic treatment protocol to the medical device 110 to enable an initial treatment of the patient; initiate the initial electronic treatment protocol with the patient; modulate the initial electronic treatment protocol to create a subsequent electronic treatment protocol, wherein the modulation of the initial electronic treatment protocol is determined by at least one from the set of: measures of patient discomfort and values from treatment history; communicate the subsequent electronic treatment protocol to the medical device 110 to enable subsequent treatment of the patient; and initiate the subsequent electronic treatment protocol with the patient.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method for administering treatment of transcranial neuromodulation (TNM) to the brain of a human patient suffering from depression to treat depression in said human patient, comprising the following steps:

providing the patient with a TNM device configured to deliver TNM to one or more stimulation locations associated with depression on a head of the patient, the TNM device having at least one TMS coil, wherein the TNM device is configured to:

receive an initial TNM treatment protocol;

verify that a placement of the at least one TMS coil on the human patient conforms to at least: an anatomical location, an orientation, a target rotation, and an angle of incidence of the initial TNM treatment protocol; and upon verification, activate the TNM device to perform the initial TNM treatment protocol on the human patient.

2. The method of claim 1, wherein the initial TNM treatment protocol is determined by at least one from the set of patient authentication, device authentication, operator authentication, location authentication, delivery schedule, session numbers, delivery hardware, stimulation target location, stimulation target rotation, stimulation intensity, stimulation pattern, pulse waveform, angle of incidence, sensor target location(s), sensor target rotations, sensor sampling rate, wavelength(s), carrier frequency, sensor type, assessment schedule, and assessment type(s).

3. The method of claim 1, wherein the initial TNM treatment protocol includes at least one parameter taken from the set of: pulse amplitude, pulse sequence timing, total number of pulses, and stimulation target.

4. The method of claim 1, wherein the initial TNM protocol originates from a central server with which the TNM device is in contact.

5. The method of claim 4, wherein the parameters of the initial TNM protocol are stipulated by a human.

6. The method of claim 5, wherein the human is a health care provider.

7. The method of claim 4, wherein the parameters of the initial TNM protocol are selected from a finite list of preset protocols.

8. The method of claim 1, wherein the initial TNM protocol is created on a user interface in communication with the TNM device.

9. The method of claim 8, wherein parameters of the initial TNM protocol are stipulated by a human.

10. The method of claim 9, wherein the human is a health care provider.

11. The method of claim 1, wherein the initial TNM protocol is extended by increasing a total number of sessions.

12. The method of claim 11, wherein the initial TNM protocol is provided by a central server with which the TNM device is in contact.

13. The method of claim 12, wherein the parameters of the initial TNM protocol are provided by a human.

14. The method of claim 13, wherein the human is a health care provider.

15. The method of claim 11, wherein the number of sessions is determined by an algorithm on a central server, the TNM device, or both, based on at least one of: a patient's or other patients' treatment history, patient psychological scales and questionnaires, and a patient's psychological medical records.

16. The method of claim 1, wherein at least a portion of a control of the treatment is controlled remotely over a communications network by a human.

17. The method of claim 1, wherein the TNM device is further configured to verify that an identity of the human patient conforms to the initial TNM treatment protocol.

18. A method for administering treatment of transcranial neuromodulation (TNM) to the brain of a human patient suffering from depression to treat depression in said human patient, comprising the steps of:

providing the patient with a TNM medical device configured to deliver transcranial neuromodulation (TNM) to the head of the patient, the TNM device having at least one TMS coil, wherein the TNM device is in communication with an Electronic Control Unit (ECU) having a processor and computer-readable memory, and wherein the ECU is configured to receive communication from the TNM device;

verifying that a placement of the at least one TMS coil at one or more stimulation locations on the head of the human patient conforms to at least: an anatomical location, an orientation, a target rotation, and an angle of incidence of an initial TNM treatment protocol; and upon verification, performing the initial TNM treatment protocol on the human patient, wherein an amplitude of one or more pulses from the TNM device is a function of the delivered amplitude of prior calibration and treatment pulses of that patient, and optionally, of other patients.

19. The method of claim 18, further comprising the step of verifying that an identity of the human patient conforms to the initial TNM treatment protocol.

* * * * *